US011020456B2

(12) United States Patent
Hunter et al.

(10) Patent No.: US 11,020,456 B2
(45) Date of Patent: Jun. 1, 2021

(54) METHODS FOR MODULATING AN INFLAMMATORY RESPONSE

(71) Applicant: THE TRUSTEES OF THE UNIVERSITY OF PENNSYLVANIA, Philadelphia, PA (US)

(72) Inventors: Christopher A. Hunter, Philadelphia, PA (US); Alejandro Villarino, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 246 days.

(21) Appl. No.: 15/883,879

(22) Filed: Jan. 30, 2018

(65) Prior Publication Data
US 2018/0161397 A1 Jun. 14, 2018

Related U.S. Application Data

(60) Division of application No. 14/256,398, filed on Apr. 18, 2014, now Pat. No. 9,913,879, which is a continuation of application No. 10/768,744, filed on Feb. 2, 2004, now abandoned.

(60) Provisional application No. 60/519,074, filed on Nov. 10, 2003, provisional application No. 60/444,494, filed on Jan. 31, 2003.

(51) Int. Cl.
*A61K 38/20* (2006.01)
*C07K 16/28* (2006.01)
*A61K 39/00* (2006.01)
*A61P 35/00* (2006.01)
*A61P 35/02* (2006.01)
*A61P 35/04* (2006.01)

(52) U.S. Cl.
CPC ............ *A61K 38/20* (2013.01); *A61K 38/208* (2013.01); *C07K 16/2866* (2013.01); *A61K 2039/505* (2013.01); *C07K 2317/76* (2013.01); Y02A 50/30 (2018.01)

(58) Field of Classification Search
None
See application file for complete search history.

(56) References Cited

U.S. PATENT DOCUMENTS

| | | | |
|---|---|---|---|
| 5,686,575 | A | 11/1997 | Prince et al. |
| 7,074,397 | B1 | 7/2006 | Matthews et al. |
| 2002/0164609 | A1 | 11/2002 | Timans et al. |
| 2004/0234522 | A1 | 11/2004 | Desauvage et al. |

FOREIGN PATENT DOCUMENTS

| | | | |
|---|---|---|---|
| WO | 9725425 | A1 | 7/1997 |
| WO | 9902552 | A2 | 1/1999 |
| WO | 0129070 | A8 | 9/2001 |
| WO | 2004069173 | A2 | 8/2004 |
| WO | 2005079848 | A9 | 12/2006 |

OTHER PUBLICATIONS

UniProt Accession No. Q6UWB1, IL27RA_human ,1998.
UniProt Accession No. Q14213, IL-27B_human ,2002.
Afkarian, et al.,T-bet is a STAT1-induced regulator of IL-12R expression in naïve CD4+ T cells, 2002, Nat Immunol 3:549-557 (Abstract).
AGA Institute, et al.,Abstacts of the AGA Institute, Gastroenterology 130(4) ,2006 ,A1-A747.
Agenllo, et al.,Cytokines and transcription factors that regulate T helper cell differentiation: new players and new insights, J Clin Immunol. 23(3) ,2003 ,147-161.
Alexander, et al.,SOCS1 is a critical inhibitor of interferon gamma signaling and prevents the potentially fatal neonatal actions of this cytokine, Cell. 98(5) ,1999 ,597-608.
Altara, et al.,Impairment of mycobacterial immunity in human interleukin-12 receptor deficiency, Science. 280 (5368) ,1998 ,1432-1435.
Artis, et al.,Differential requirement for NF-kappa B family members in control of helminth infection and intestinal inflammation, J Immunol. 169(8) ,2002 ,4481-4487.
ARTIS, et al.,Tumor necrosis factor alpha is a critical component of interleukin 13-mediated protective T helper cell type 2 responses during helminth infection, J Exp Med. 190(7) ,1999 ,953-962.
Bancroft, et al.,A critical role for IL-13 in resistance to intestinal nematode infection, J Immunol. 160 (7) ,1998 ,3453-3461.
Batten, et al.,Interleukin 27 limits autoimmune encephalomyelitis by suppressing the development of interleukin 17-producing T cells, Nat Immunol. 7(9) ,2006 ,929-936.
Batten, et al.,The biology and therapeutic potential of interleukin 27, J Mol Med (Berl). 85(7) ,2007 ,661-672.
Becker, et al.,Stepwise regulation of TH1 responses in autoimmunity: IL-12-related cytokines and their receptors, Inflamm Bowel Dis. 11(8) ,2005 ,755-764.
Brombacher, et al.,Novel IL-12 family members shed light on the orchestration of Th1 responses, Trends Immunol. 24(4) ,2003 , 207-212.
Cai, et al.,Identification of STAT4-dependent and independent mechanisms of resistance to Toxoplasma gondii, J Immunol. 165(5) , 2000 ,2619-2627.
Chen, et al.,Development of Th1-type immune responses requires the type I cytokine receptor TCCR, Nature. 407 (6806) ,2000 , 916-920.

(Continued)

*Primary Examiner* — Gary B Nickol
*Assistant Examiner* — Jegatheesan Seharaseyon
(74) *Attorney, Agent, or Firm* — Saul Ewing Arnstein & Lehr LLP; Kathryn Doyle; Justin Crotty

(57) ABSTRACT

The inventive subject matter relates to novel methods for modulating an immune response in an animal, which comprises administering to said animal an effective amount of an agent that increases IL-27R/WSX-1 activity. Further, the inventive subject matter relates to pharmaceutical compositions comprising an effective amount of an agent that increases IL-27R/WSX-1 activity.

5 Claims, 15 Drawing Sheets

(56) References Cited

OTHER PUBLICATIONS

Chu, et al., Failure to suppress the expansion of the activated CD4 T cell population in interferon gamma-deficient mice leads to exacerbation of experimental autoimmune encephalomyelitis, J Exp Med. 192(1) ,2000 ,123-128.
Cousens, et al.,Interferon-alpha/beta inhibition of interleukin 12 and interferon-gamma production in vitro and endogenously during viral infection, Proc Natl Acad Sci U S A. 94(2) ,1997 ,634-639.
Dalton, et al.,Interferon gamma eliminates responding CD4 T cells during mycobacterial infection by inducing apoptosis of activated CD4 T cells, J Exp Med. 192(1) ,2000 ,117-122.
De Jong, et al.,Severe mycobacterial and Salmonella infections in interleukin-12 receptor-deficient patients, Science. 280(5368) , 1998 ,1435-1438.
Dela Cruz, et al.,Antibody-cytokine fusion proteins: innovative weapons in the war against cancer, Clin Exp Med. 4 (2) ,2004 , 57-64.
Denkers, et al.,Regulation and function of T-cell-mediated immunity during Toxoplasma gondii infection, Clin Microbiol Rev. 11(4) ,1998 ,569-588.
Devergne, et al.,A novel interleukin-12 p40-related protein induced by latent Epstein-Barr virus infection in B lymphocytes, J Virol. 70(2) ,1996 ,1143-1153.
Devergne, et al.,Epstein-Barr virus-induced gene 3 and the p35 subunit of interleukin 12 form a novel heterodimeric hematopoietin, Proc Natl Acad Sci U S A. 94(22) ,1997 ,12041-12046.
Diehl, et al.,Inhibition of Th1 differentiation by IL-6 is mediated by SOCS1, Immunity. 13(6) ,2000 ,805-815.
Diveu, et al.,Cytokines that regulate autoimmunity, Curr Opin Immunol. 20(6) ,2008 ,663-668.
Diveu, et al.,IL-27 blocks RORc expression to inhibit lineage commitment of Th17 cells, J Immunol. May 1, 2009;182 (9) , 2009 ,5748-5756.
Doyle et al.,Induction of cytotoxic T lymphocyte antigen 4 (CTLA-4) restricts clonal expansion of helper T cells, J Exp Med. Oct. 1, 2001;194(7) ,2001 ,893-902.
Else, et al.,Cytokine-mediated regulation of chronic intestinal helminth infection, J Exp Med. 179(1) ,1994 ,347-351.
Ely, et al.,Augmentation of the CD8+ T cell response by IFN-gamma in IL-12-deficient mice during Toxoplasma gondii infection, J Immunol. May 1, 1999;162(9) ,1999 ,5449-5454.
Fitzgerald, et al.,Suppression of autoimmune inflammation of the central nervous system by interleukin 10 secreted by interleukin 27-stimulated T cells, Nat Immunol. 8(12) ,2007 ,1372-1379.
Fitzgerald, et al.,Suppressive effect of IL-27 on encephalitogenic Th17 cells and the effector phase of experimental autoimmune encephalomyelitis, J Immunol. Sep. 1, 2007;179(5) ,2007 ,3268-3275.
Fitzgerald, et al.,Therapeutic potential of IL-27 in multiple sclerosis?, Expert Opin Biol Ther. 9(2) ,2009 ,149-160.
Fujimoto, et al.,A regulatory role for suppressor of cytokine signaling-1 in T(h) polarization in vivo, Int Immunol. 14 (11) , 2002 ,1343-1350.
Gabay, et al.,The biological and clinical importance of the 'new generation' cytokines in rheumatic diseases, Arthritis Res Ther. 11(3) ,2009 ,230.
Gazzinelli, et al.,In the absence of endogenous IL-10, mice acutely infected with Toxoplasma gondii succumb to a ethal immune response dependent on CD4+ T cells and accompanied by overproduction of IL-12, IFN-gamma and TNF-alpha, J Immunol. 157(2) ,1996 ,798-805.
Gazzinelli, et al.,Interleukin 12 is required for the T-lymphocyte-independent induction of interferon gamma by an Intracellular parasite and induces resistance in T-cell-deficient hosts, Proc Natl Acad Sci U S A. 90 (13) ,1993 ,6115-6119.
Gazzinelli, et al.,Parasite-induced IL-12 stimulates early IFN-gamma synthesis and resistance during acute infection with Toxoplasma gondii, J Immunol. 153(6) ,1994 ,2533-2543.
Goriely, et al.,The interleukin-12 family: new players in transplantation immunity?, Am J Transplant. 7 (2) ,2007 ,278-284.

Guo, et al.,The type I IFN induction pathway constrains Th17-mediated autoimmune inflammation in mice, J Clin Invest. 118(5) ,2008 ,1680-1690.
Hamano, et al.,WSX-1 is required for resistance to Trypanosoma cruzi infection by regulation of proinflammatory cytokine production., Immunity. Nov. 2003;19(5) ,2003 ,657-667.
Helmby, et al.,Interleukin (IL)-18 promotes the development of chronic gastrointestinal helminth infection by downregulating IL-13, J Exp Med. 94(3) ,2001 ,355-364.
Hibbert, et al.,IL-27 and IFN-alpha signal via Stat1 and Stat3 and induce T-Bet and IL-12Rbeta2 in naive T cells., J Interferon Cytokine Res. 23(9) ,2003 ,513-522.
Ho, et al.,Transcription: tantalizing times for T cells, Cell. 109 Suppl. ,2002 ,S109-120.
Hosken, et al.,IL-27 promotes TH1 Developments and Inflammation Partly by Affecting Regulatory T Cells, Eur Cytokine Netw., 17 ,2006 ,80.
Hunter, et al.,New IL-12-family members: IL-23 and IL-27, cytokines with divergent functions, Nat Rev Immunol. 5 (7) ,2005 ,521-531.
Kastelein, et al.,Discovery and biology of IL-23 and IL-27: related but functionally distinct regulators of inflammation, Annu Rev Immunol. 25 ,2007 ,221-242.
Kreydiyyeh, et al.,Cytokine interferon/mode of action, Eur. Cytokine Netw. 17 ,2006 ,73-81(Abstrct Only).
Lee, et al.,STAT1 affects lymphocyte survival and proliferation partially independent of its role downstream of IFN-gamma, J Immunol. 164(3) ,2000 ,1286-1292.
Liesenfeld, et al.,Association of CD4+ T cell-dependent, interferon-gamma-mediated necrosis of the small intestine with genetic susceptibility of mice to peroral infection with Toxoplasma gondii, J Exp Med. 184(2) ,1996 ,597-607.
Lighvani, et al.,T-bet is rapidly induced by interferon-gamma in lymphoid and myeloid cells, Proc Natl Acad Sci U S A 98 , 2001 ,15137-15142.
Lucas, et al.,IL-27 regulates IL-12 responsiveness of naive CD4+ T cells through Stat1-dependent and -independent mechanisms, Proc Natl Acad Sci U S A. 100(25) ,2003 ,15047-15052.
McKenzie, et al.,A distinct role for interleukin-13 in Th2-cell-mediated immune responses, Curr Biol. 8 (6) ,1998 ,339-342.
Miyazaki, et al.,Amelioration of delayed-type hypersensitivity responses by IL-27 administration., Biochem Biophys Res Commun. 373(3) ,2008 ,397-402.
Mullen, et al.,Role of T-bet in commitment of TH1 cells before IL-12-dependent selection, Science 292 ,2001 ,1907-1910.
Murphy, et al.,The lineage decisions of helper T cells, Nat Rev Immunol. 2(12) ,2002 ,933-944.
Naka, et al.,SOCS-1/SSI-1-deficient NKT cells participate in severe hepatitis through dysregulated cross-talk inhibition of IFN-gamma and IL-4 signaling in vivo, Immunity. May 2000;14(5) , 2001 ,535-454.
Nakagawa, et al.,SOCS-1 participates in negative regulation of LPS responses, Immunity. 17(5) ,2002 ,677-687.
Neyer, et al.,Role of interleukin-10 in regulation of T-cell-dependent and T-cell-independent mechanisms of resistance to Toxoplasma gondii, Infect Immun. 65(5) ,1997 ,1675-1682.
Nguyen, et al.,Interferon alpha/beta-mediated inhibition and promotion of interferon gamma: STAT1 resolves a paradox, Nat Immunol. 1(1) ,2000 ,70-76.
Niedbala, et al.,Interleukin 27 attenuates collagen-induced arthritis, Ann Rheum Dis. 67(10) ,2008 ,1474-1479.
Nieuwenhuis, et al., Disruption of T helper 2-immune responses in Epstein-Barr virus-induced gene 3-deficient mice, Proc Natl Acad Sci U S A. 99(26) ,2002 ,16951-16956.
O'Shea, et al.,Cytokine signaling in 2002: new surprises in the Jak/Stat pathway, Cell. 109 Suppl ,2002 ,S121-31.
Paya, et al.,Inhibition of Theiler's virus-induced demyelination in vivo by tumor necrosis factor alpha, Int Immunol. 2(9) , 1990 ,909-913.
Pflanz, et al.,IL-27, a heterodimeric cytokine composed of EBI3 and p28 protein, induces proliferation of naive CD4+ T cells, Immunity. Jun. 2002;16(6) ,2002 ,779-790.

(56) References Cited

OTHER PUBLICATIONS

Pflanz, et al.,WSX-1 and glycoprotein 130 constitute a signal-transducing receptor for IL-27, J Immunol. 172(4) ,2004 ,2225-2231.

Robinson, et al.,Further checkpoints in Th1 development., Immunity. 16(6) ,2002 ,755-758.

Scharton-Kersten, et al.,In the absence of endogenous IFN-gamma, mice develop unimpaired IL-12 responses to Toxoplasma gondii while failing to control acute infection., J Immunol. Nov. 1, 1996;157 (9) ,1996 ,4045-4054.

Scheller, et al.,No inhibition of IL-27 signaling by soluble gp130, Biochem Biophys Res Commun. 326(4) ,2005 ,724-728.

Seita, et al.,Interleukin-27 directly induces differentiation in hematopoietic stem cells, Blood. 111(4) ,2008 ,1903-1912.

Seki, et al.,SOCS-3 regulates onset and maintenance of T(H)2-mediated allergic responses, Nat Med. 9(8) ,2003 ,1047-1054.

Shimizu, et al.,Membranous glomerulonephritis development with Th2-type immune deviations in MRL/lpr mice deficient for IL-27 receptor (WSX-1), J Immunol. 175(11) ,2005 ,7185-7192.

Sicotte, et al.,Onset of multiple sclerosis associated with anti-TNF therapy, Neurology. 57(10) ,2001 ,1885-1888.

Sprecher, et al.,Cloning and characterization of a novel class I cytokine receptor, Biochem Biophys Res Commun. 246(1) , 1998 ,82-90.

Stetson, et al.,Rapid expansion and IL-4 expression by Leishmania-specific naive helper T cells in vivo, Immunity.17(2) ,2002 ,191-200.

Stumhofer, et al.,Advances in understanding the anti-inflammatory properties of IL-27, Immunol Lett. 117(2) ,2008 ,123-130.

Szabo, et al.,Molecular mechanisms regulating Th1 immune responses, Annu Rev Immunol. 21 ,2003 ,713-758.

Takeda, et al.,Cutting edge: role of IL-27/WSX-1 signaling for induction of T-bet through activation of STAT1 during Initial Th1 commitment, J Immunol. 170(10) ,2003 ,4886-4890.

Thomson, et al.,The Cytokine Handbook, Fourth Edition, vol. 1, Academic Press, San Diego ,2003 ,281.

Trinchieri, et al.,Interleukin-12 and the regulation of innate resistance and adaptive immunity, Nat Rev Immunol. 3(2) ,2003 ,133-146.

Trinchieri, et al.,The IL-12 family of heterodimeric cytokines: new players in the regulation of T cell responses, Immunity. 19(5) , 2003 ,641-644.

Vandenbroeck, et al.,Inhibiting cytokines of the interleukin-12 family: recent advances and novel challenges, J Pharm Pharmacol. 56(2) ,2004 ,145-160.

Villarino, et al.,IL-27 limits IL-2 production during Th1 differentiation., J Immunol. 176(1) ,2006 ,237-247.

Villarino, et al.,The IL-27R (WSX-1) is required to suppress T cell hyperactivity during infection, Immunity. 19(5) ,2003 ,645-655.

Villarino, et al.,Understanding the pro- and anti-inflammatory properties of IL-27, J Immunol. 173(2) ,2004 ,715-720.

Welte, et al.,STAT3 deletion during hematopoiesis causes Crohn's disease-like pathogenesis and lethality: a critical role of STAT3 in innate immunity, Proc Nall Acad Sci U S A. 100(4) ,2003 ,1879-1884.

Yoo, et al.,Specitic ablation of Stat3beta distorts the pattern of Stat3-responsive gene expression and impairs recovery from endotoxic shock, Cell. 108(3) ,2002 ,331-344.

Yoshida, et al.,Interleukin 27: a double-edged sword for offense and defense, J Leukoc Biol. 86(6) ,2009 ,1295-1303.

Yoshida, et al.,Regulation of immune responses by interleukin-27, Immunol Rev. 226 ,2008 ,234-247.

Yoshida, et al.,WSX-1 is required for the initiation of Th1 responses and resistance to L. major infection, Immunity. Oct. 2001;15 (4) ,2001 ,569-578.

METHODS FOR MODULATING AN INFLAMMATORY RESPONSE

This application is a divisional of U.S. patent application Ser. No. 14/256,398, filed Apr. 18, 2014, now U.S. Pat. No. 9,913,879, which is a continuation of U.S. patent application Ser. No. 10/768,744 filed Feb. 2, 2004, now abandoned, which claims the benefit of U.S. Provisional Patent Application No. 60/444,494, filed Jan. 31, 2003, and U.S. Provisional Patent Application No. 60/519,074, filed Nov. 10, 2003, the contents of which are hereby incorporated by reference in their entirety.

This invention was made with government support under grant numbers AI041158 and AI042334, and AI035914 awarded by the National Institutes of Health. The government has certain rights in the invention.

BACKGROUND OF THE INVENTION

1. Field of Invention

The inventive subject matter relates to novel methods for modulating an immune response in an animal, which comprises administering to said animal an effective amount of an agent that increases IL-27R/WSX-1 activity. Further, the inventive subject matter relates to pharmaceutical compositions comprising an effective amount of an agent that increases IL-27R/WSX-1 activity.

2. Background

WSX-1 is a class I cytokine receptor that is homologous to the ß2 chain of the IL-12R in both sequence and structure. This receptor is highly expressed by resting/naive $CD4^+$ T cells and $CD8^+$ T cells. Recent studies have identified IL-27, heterodimeric cytokine composed of the subunits EBI3 and IL-27p28, as the ligand for WSX-1. EBI3, a member of the class I cytokine receptor family, shares significant structural homology to IL-12p40, and IL-27p28 is closely related to IL-12p35. In addition to the structural similarity between the IL-12/IL-12R and IL-27/WSX-1 ligand/receptor pairs, there are also reports that show functional similarity. While the IL-12R plays a critical role in the development of Th1 type responses, it has been reported that WSX-1 deficient cells have impaired IFN-γ production during early Th1 differentiation. Moreover, recombinant IL-27, like IL-12, can enhance Th1 differentiation in highly purified naive helper T cells. As a consequence of these studies, an early consensus emerged that IL-27/WSX-1 was, like the IL-12/IL-12R interaction, an important factor in the initial differentiation of Th1 responses.

Although recent studies have described IL-27 and its receptor, WSX-1, as promoters of Th1 differentiation in naive $CD4^+$ T cells, Applicants have determined that signaling through this receptor is involved in limiting the intensity and duration of T cell activity. When WSX-1-deficient mice are infected with the intracellular pathogen *Toxoplasma gondii*, they establish protective T cell responses, characterized by production of inflammatory cytokines and control of parasite replication. However, infected $WSX-1^{-/-}$ mice are unable to downregulate these protective responses, and develop a lethal, T cell-mediated inflammatory disease.

Contrary to the previous consensus understanding, we have demonstrated that WSX-1-deficient mice infected with *T. gondii* are able to develop a strong Th1 type response and control parasite replication, but are unable to downregulate this protective response and develop a lethal, T cell-mediated inflammatory disease. This pathology was characterized by the excessive production of IFN-γ, persistence of highly activated T cells, and enhanced T cell proliferation in vivo. The phenotype could be recapitulated in vitro as Th1 polarization of $WSX-1^{-/-}$ $CD4^+$ T cells led to increased proliferation and IFN-γ secretion. However, these studies also confirmed that, under nonpolarizing conditions, WSX-1 is required for optimal IFN-γ production. Further analysis revealed that exogenous IL-27 can activate STAT1, STAT3, and STAT5: STAT family members that have traditionally been associated with cellular activation but have also recently been linked with the inhibition of immune functions. Together, these findings demonstrate that WSX-1 is not required for the generation of IFN-γ-mediated immunity to *T. gondii* and identify a novel function for WSX-1 as a potent antagonist of T cell-mediated immune hyperactivity.

Thus, we have found a method for treating immune hyperreactivity, wherein the method comprises administering an effective amount of an agent that increases WSX-1 activity. Such agents include IL-27, an active fragment thereof, an agonistic antibody that binds to an epitope on WSX-1 and, as WSX-1 is part of the heterodimeric receptor IL-27R along with IL-27RPP, an agonistic antibody that binds to an epitope on dimeric IL-27R, and an agonistic antibody that binds to an epitope on IL-27RPP. Such agents may also be used to suppress the function of polarized T cells, to treat Th1-mediated disease, to treat Th2-mediated disease, to treat IFN-γ mediated disease, to modulate the response of non-lymphoid cells (e.g., MAST cells) to Immunoglobulin E (IgE), and to treat IgE-mediated disease (e.g., asthma, allergy, and the like). Such agents may be used to treat a number of autoimmune diseases, as further disclosed in detail below.

We have also found a method for increasing immune response, which is useful in treating patients with suppressed immune systems. Such immunosuppression can result, for example, from disease or from chemotherapy. This method comprises administering an effective amount of an agent that binds to IL-27 and/or IL-27R/WQSX-1 and prevents activation of IL-27R by IL-27. Such agents include an antibody that binds to IL-27, an antibody that binds to EB13 (a subunit of IL-27), an antibody that binds to IL27p28 (also a subunit of IL-27), a soluble form of WSX-1, a soluble form of dimeric IL-27R, a soluble form of IL-27RPP, and a non-activating IL-27R/WSX-1 ligand. Such agents may be used to treat a number of diseases and conditions related to immunosuppression, as further detailed herein below.

Further in accordance with the present invention, also provided is a method for screening for molecules useful in the methods described hereinabove, which comprises (a) treating cells comprising IL-27 receptor with a test agent; (b) determining any effect of the test agent on IL-27 receptor activity.

SUMMARY OF THE INVENTION

The inventive subject matter relates to a method for modulating an immune response in an animal in need thereof, which comprises administering to said animal an effective amount of an IL-27R/WSX-1 ligand.

The inventive subject matter further relates to a method for modulating a T-helper cell mediated immune response in an animal in need thereof, which comprises administering to said animal an effective amount of an IL-27R/WSX-1 ligand.

method for modulating an interferon-γ mediated immune response in an animal in need thereof, which comprises administering to said animal an effective amount of an IL-27R/WSX-1 ligand.

The inventive subject matter further relates to a method for treating immune hyperactivity in an animal in need thereof, which comprises administering to said animal an effective amount of an IL-27R/WSX-1 ligand.

The inventive subject matter further relates to a method for treating a T-helper cell mediated disorder in an animal in need thereof, which comprises administering to said animal an effective amount of an IL-27R/WSX-1 ligand.

The inventive subject matter further relates to a method for modulating a T-helper cell mediated immune response in an animal in need thereof, which comprises administering to said animal an effective amount of an IL-27R/WSX-1 ligand.

The inventive subject matter further relates to a pharmaceutical composition comprising:
  (i) an effective amount of an IL-27R/WSX-1 ligand; and
  (ii) a pharmaceutically acceptable carrier.

The inventive subject matter further relates to a method of treating immune hyperreactivity, which comprises administering an effective amount of an agent that increases WSX-1 activity.

The inventive subject matter further relates to a method of suppressing polarized T cells, which comprises administering an effective amount of an agent that increases WSX-1 activity.

The inventive subject matter further relates to a method of treating Th1-mediated disease, which comprises administering an effective amount of an agent that increases WSX-1 activity.

The inventive subject matter further relates to a method of treating Th2-mediated disease, which comprises administering an effective amount of an agent that increases WSX-1 activity.

The inventive subject matter further relates to a method of treating IFN-mediated disease, which comprises administering an effective amount of an agent that increases WSX-1 activity.

The inventive subject matter further relates to a method of treating IgE-mediated disease, which comprises administering an effective amount of an agent that increases WSX-1 activity.

The inventive subject matter further relates to a method of treating asthma, which comprises administering an effective amount of an agent that increases WSX-1 activity.

The inventive subject matter further relates to a method of treating allergy, which comprises administering an effective amount of an agent that increases WSX-1 activity.

DETAILED DESCRIPTION OF THE INVENTION

Definitions

Figures 1A, 1B, 1C, 1D:
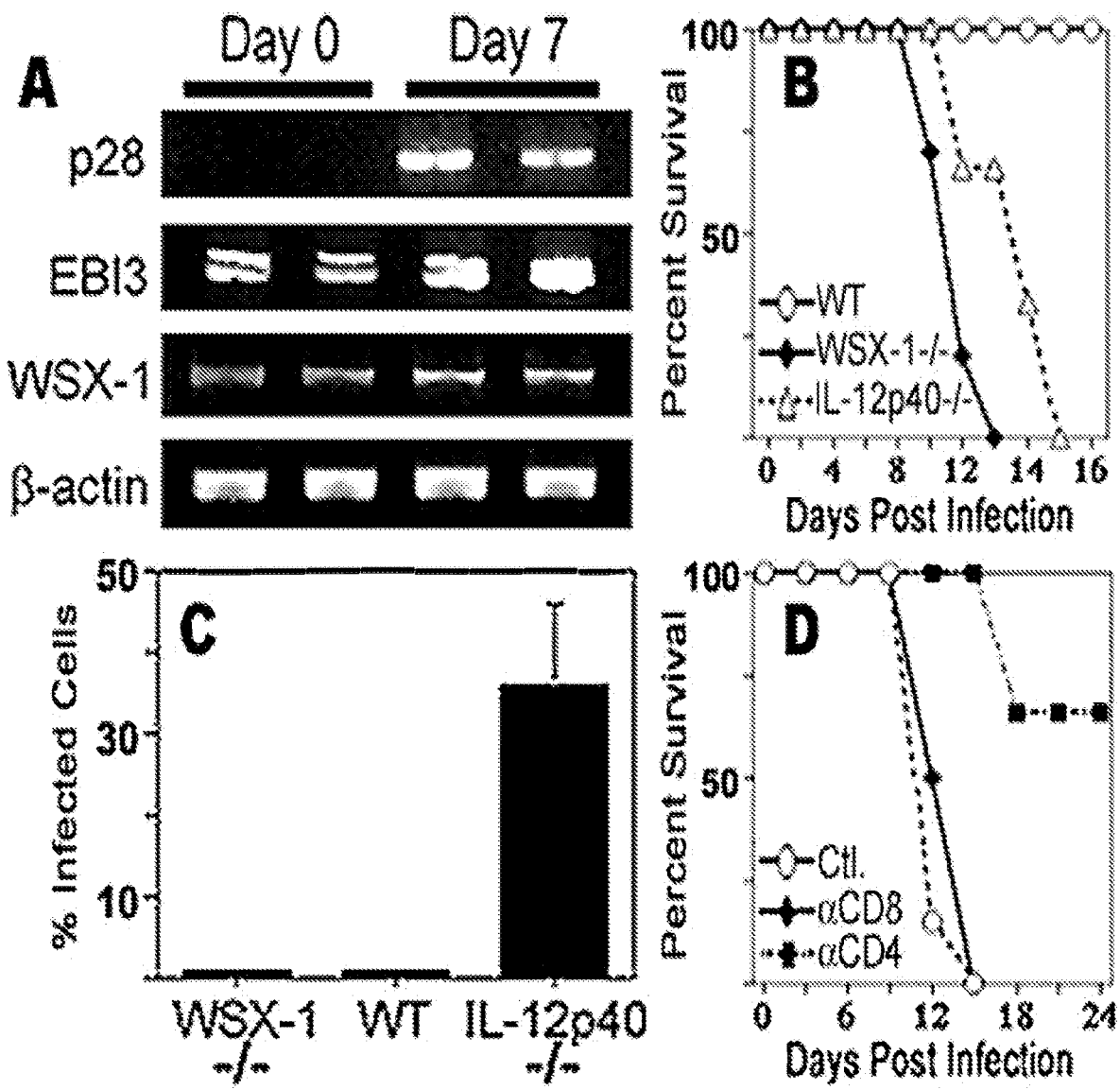
FIG. 1A is a photograph which depicts a protein gel showing expression levels of mRNA for IL-27p28, EBI3, WSX-1, and β-actin.
FIG. 1B is a graph which depicts survival times of wild type, WSX-1$^{-/-}$, and IL-12p40$^{-/-}$ mice infected with $T.$ $gondii$.
FIG. 1C is a graph which depicts percentage of cells infected with $T.$ $gondii$.
FIG. 1D is a graph which depicts survival of WSX-1$^{-/-}$ mice infected with $T.$ $gondii$.
Figures 1E, 1F, 1G, 1H:
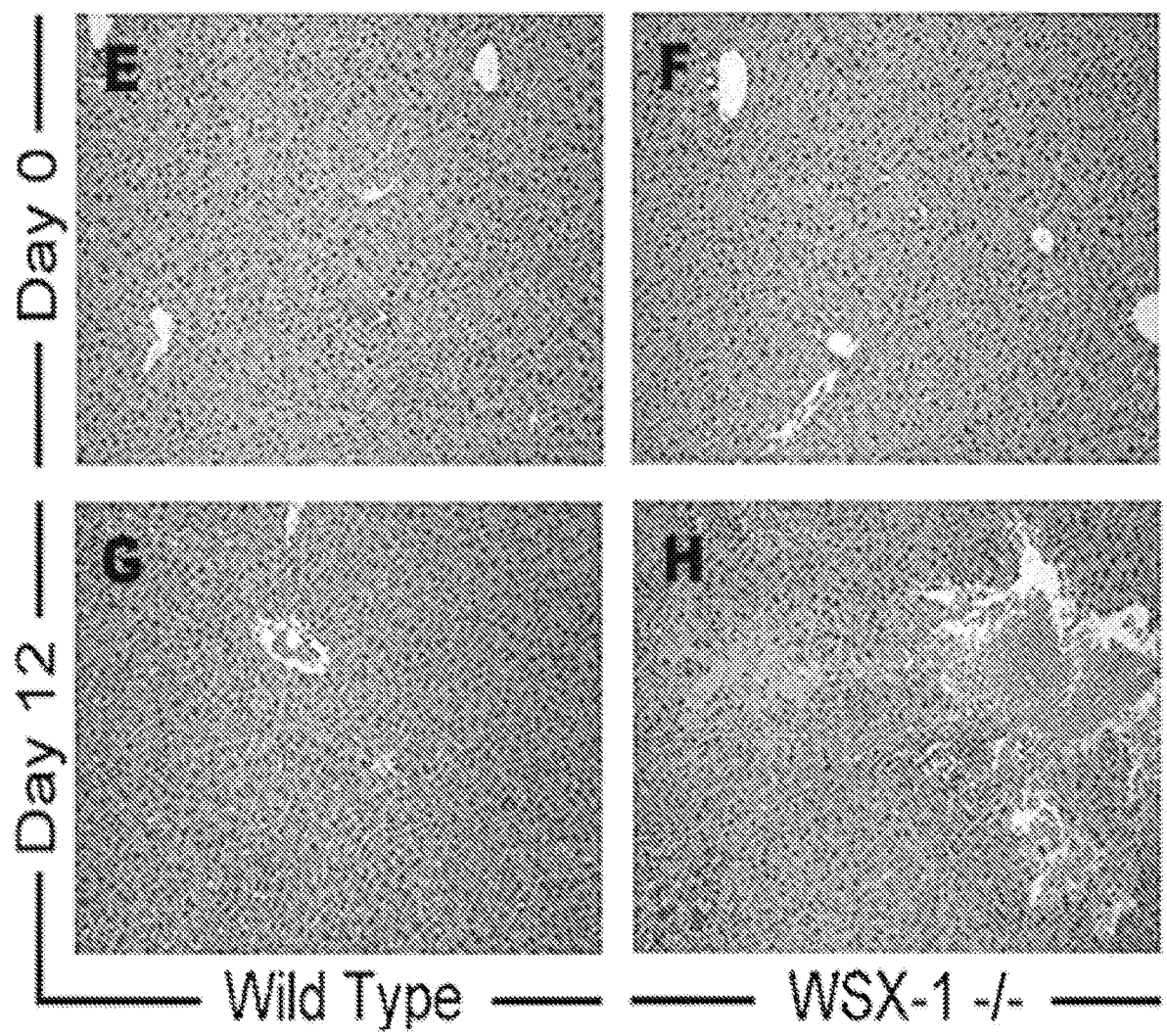
FIGS. 1E-H are histological slides which depict liver tissue of wild type and WSX-1$^{-/-}$ animals before infection and after being infected for 12 days.

Unless otherwise required by context, singular terms shall include pluralities and plural terms shall include the singular.

Throughout this document, reference is made to the terms "WSX-1", "IL-27R", and "IL-27R/WSX-1". It is to be understood that these terms are used interchangeably to refer to the receptor for IL-27.

The term "ligand" as used herein refers to a molecule, or a domain of a molecule, which is bound or able to bind selectively and stoichiometrically, either covalently or not, to one or more specific sites on another molecule. Non-limiting examples of ligands include an antibody and its antigen, a hormone and its receptor, and an enzyme and its substrate.

Terms Related to Treatment of Disease

The term "patient" includes human and animal subjects. The term "modulating" refers to regulating or adjusting the degree of activity of a process or the degree of an effect. "Modulating" includes activation, amplification, attenuation, and suppression.

The term "effecting" refers to the process of producing an effect on biological activity, function, health, or condition of an organism in which such biological activity, function, health, or condition is maintained, enhanced, diminished, or treated in a manner which is consistent with the general health and well-being of the organism.

The term "enhancing" the biological activity, function, health, or condition of an organism refers to the process of augmenting, fortifying, strengthening, or improving.

A "treatment" or "treating" of a disorder, condition, or disease (including an autoimmune disease), encompasses alleviation of at least one symptom thereof, a reduction in the severity thereof, or the delay or prevention of progression to a more serious disease that occurs with some frequency following the treated disease or disorder. Treatment need not mean that the disease is totally cured. A useful therapeutic agent needs only to reduce the severity of a disease, reduce the severity of a symptom or symptoms associated with the disease or its treatment, or provide improvement to a patient's quality of life, or delay the onset of a more serious disease that can occur with some frequency following the treated disease, disorder, or condition. For example, if the disease is rheumatoid arthritis, a therapeutic agent may decrease swelling of joints, reduce the number of joints affected, or delay or inhibit bone loss. An SLE patient can have symptoms such as skin lesions, fever, weakness, arthritis, lymphadenopathy, pleurisy, pericarditis, and/or anemia, among others. Such symptoms can be assessed by any of a number of conventional techniques including, for example, visual observation, photography, measurement of temperature, grip strength, or joint size, and/or microscopic examination of blood to determine the concentration of red blood cells. The invention encompasses a method for treatment comprising administering to a patient an agent in an amount and for a time sufficient to induce a sustained improvement over baseline of an indicator that reflects the severity of a particular disease, disorder, or condition or the severity of symptoms caused thereby or to delay or prevent the onset of a more serious disease that follows the treated disease, disorder, or condition in some or all cases. The invention does not exclude possible treatment with other therapeutic agents before, after, and/or during treatment with the agents described herein.

A disease or medical condition is considered to be a "Th1-mediated disease" or "Th1-mediated disorder" if the naturally-occurring or experimentally-induced disease or medical condition is associated with proliferation or increased differentiation of Th1 cells. Th1-mediated disease can be identified by (1) levels of Th1 cells that exceed those normally found in a human, animal, or cell culture; (2) pathological findings associated with the disease or medical condition that can be mimicked experimentally in animals by administration of agents that upregulate proliferation or differentiation of Th1 cells; or (3) a pathology induced in experimental animal models of the disease or medical condition can be inhibited or abolished by treatment with agents that inhibit the proliferation or differentiation of Th1 cells. In most Th1-mediated diseases, at least two of the three conditions are met.

A non-exclusive list of acute and chronic Th1-mediated diseases includes but is not limited to the following: acute pancreatitis; amyelolateroschlerosis (ALS); Alzheimer's disease; cachexia/anorexia, including AIDS-induced cachexia; asthma and other pulmonary diseases; atherosclerosis; autoimmune vasculitis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML or CML)

and other leukemias, as well as tumor metastasis; diabetes (e.g., insulin-dependent diabetes); endometriosis; fever; fibromyalgia; glomerulonephritis; graft versus host disease/transplant rejection; hemorrhagic shock; hyperalgesia; inflammatory bowel disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes.

A disease or medical condition is considered to be a "Th2-mediated disease" if the naturally-occurring or experimentally-induced disease or medical condition is associated with proliferation or increased differentiation of Th2 cells. Th2-mediated disease can be identified by (1) levels of Th2 cells that exceed those normally found in a human, animal, or cell culture; (2) pathological findings associated with the disease or medical condition that can be mimicked experimentally in animals by administration of agents that upregulate proliferation or differentiation of Th2 cells; or (3) a pathology induced in experimental animal models of the disease or medical condition can be inhibited or abolished by treatment with agents that inhibit the proliferation or differentiation of Th2 cells. In most Th2-mediated diseases, at least two of the three conditions are met.

A non-exclusive list of acute and chronic Th2-mediated diseases includes but is not limited to the following: acute pancreatitis; amyelolateroschlerosis (ALS); Alzheimer's disease; cachexia/anorexia, including AIDS-induced cachexia; asthma and other pulmonary diseases; atherosclerosis; autoimmune vasculitis; chronic fatigue syndrome; Clostridium associated illnesses, including Clostridium-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML or CML) and other leukemias, as well as tumor metastasis; diabetes (e.g., insulin-dependent diabetes); endometriosis; fever; fibromyalgia; glomerulonephritis; graft versus host disease/transplant rejection; hemorrhagic shock; hyperalgesia; inflammatory bowel disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes.

The term "IFN-γ mediated disease" includes, but is not limited to, inflammatory, infectious, and autoimmune diseases. An "autoimmune disease" as used herein refers to disease states and conditions wherein a patient's immune response is directed toward the patient's own constituents. For example, IFN-γ mediated diseases include, but are not limited to, Acquired Immune Deficiency Syndrome (AIDS), rheumatoid arthritis, inflammatory bowel diseases including ulcerative colitis and Crohn's disease, multiple sclerosis, Addison's disease, diabetes (type I), epididymitis, glomerulonephritis, Graves' disease, Guillain-Barre syndrome, Hashimoto's disease, hemolytic anemia, systemic lupus erythematosus (SLE), lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies, thyroiditis, and vasculitis. Because IFN-γ is a cytokine with multiple functions, including protecting the body from viral infection and regulating several aspects of the immune response, increased IFN-γ activity can contribute to several pathological conditions. The term "IFN-gamma mediated disease" also encompasses any medical condition associated with increased levels of IFN-γ or increased sensitivity to IFN-γ. Additional IFN-γ mediated diseases include: acute pancreatitis; ALS; Alzheimer's disease; cachexia/anorexia, including AIDS-induced cachexia; asthma and other pulmonary diseases; atherosclerosis; chronic fatigue syndrome; Clostridium associated illnesses, including Clostridium-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML and CML) and other leukemias, as well as tumor metastasis; fever; glomerulonephritis; graft versus host disease/transplant rejection; hemohorragic shock; inflammatory eye disease, as may be associated with, for example, corneal transplant; ischemia, including cerebral ischemia (e.g., brain injury as a result of trauma, epilepsy, hemorrhage or stroke, each of which may lead to neurodegeneration); learning impairment; multiple sclerosis; myopathies (e.g., muscle protein metabolism, esp. in sepsis); neurotoxicity (e.g., as induced by HIV); osteoporosis; pain, including cancer-related pain; Parkinson's disease; periodontal disease; neurotoxicity; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes; diabetes, including juvenile onset Type 1, diabetes mellitus, and insulin resistance (e.g., as associated with obesity); endometriosis, endometritis, and related conditions; fibromyalgia or analgesia; hyperalgesia; lung diseases (e.g., adult respiratory distress syndrome, and pulmonary fibrosis); neuroinflammatory diseases; ocular diseases and conditions, including ocular degeneration and uveitis; Pityriasis rubra pilaris (PRP); prostatitis (bacterial or non-bacterial) and related conditions; psoriasis and related conditions; pulmonary fibrosis; reperfusion injury; inflammatory conditions of a joint and rheumatic diseases including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjögren's syndrome, rheumatic fever, polychondritis and polymyalgia rheumatica and giant cell arteritis; septic shock; side effects from radiation therapy; temporal mandibular joint disease; thyroiditis; tissue transplantation or an inflammatory condition resulting from strain, sprain, cartilage damage, trauma, and orthopedic surgery.

The term "IgE-related diseases" refers to diseases, disorders, and conditions associated with increased production of Immunoglobulin E. Such diseases, disorders, and conditions comprise asthma, allergy, and the like.

The terms "WSX-1 activity" and "IL-27R activity" refer to any biological activity heretofore or hereafter found to be associated with interaction of IL-27 and its receptor, known variously as IL-27R or WSX-1. By way of example, WSX-1 activity includes, but is not limited to, resistance to infection, modulation of infection-induced cytokine production (including IFN-γ), and modulation of levels of CD4+ and CD8+ T cells as shown in the accompanying figures and the disclosed materials and methods.

The term "selective binding agent" refers to a molecule which preferentially binds a protein of interest. A selective binding agent may include a protein, peptide, nucleic acid, carbohydrate, lipid, or small molecular weight compound. Examples of proteins that are selective binding agents of the inventive subject matter include soluble receptors (i.e., proteins having all or part of the extracellular domain of a naturally occurring membrane-bound protein but not the transmembrane domain or intracellular domain); antibodies and fragments thereof; variants, derivatives and fusion proteins of antibodies and soluble receptors; peptidomimetic compounds; and organo-mimetic compounds. In a preferred embodiment, a selective binding agent is an antibody, such as polyclonal antibodies, monoclonal antibodies (mAbs), chimeric antibodies, CDR-grafted antibodies, anti-idiotypic (anti-Id) antibodies to antibodies that can be labeled in soluble or bound form, as well as fragments, regions or derivatives thereof, provided by known techniques, including, but not limited to enzymatic cleavage, peptide synthesis or recombinant techniques. The selective binding agents of the present inventive subject matter are capable of binding portions of their respective protein of interest that inhibit the binding of the protein of interest to its cognate receptor or ligand.

Assays for Selective Binding Agents

Screening methods for identifying selective binding agents which partially or completely mimic or inhibit at least one biological activity of a protein of interest (e.g., mimicking the activity of IL-27) are provided by the inventive subject matter. Inhibiting the biological activity of a protein of interest includes, but is not limited to, inhibiting binding of the protein to its cognate receptor, inhibiting the activity thereof as measured by in vitro or in vivo assays. Mimicking the biological activity of a protein of interest includes, but is not limited to, binding to the protein's cognate receptor and causing biological activity similar to the protein of interest as measured by in vitro or in vivo assays. In vitro assays include those that detect binding of the protein to its cognate receptor or ligand and may be used to screen selective binding agents for their ability to increase or decrease the rate or extent of such binding. In one type of assay, a polypeptide, such as a soluble receptor, is immobilized on a solid support (e.g., agarose or acrylic beads) and its cognate ligand is added either in the presence or absence of a selective binding agent. The extent of binding of the soluble receptor and its cognate ligand in the presence or absence of a selective binding agent present is measured. Binding can be detected by for example radioactive labeling, fluorescent labeling or enzymatic reaction.

Alternatively, the binding reaction may be carried out using a surface plasmon resonance detector system such as the BIAcore assay system (Pharmacia, Piscataway, N.J.). Binding reactions may be carried out according to the manufacturer's protocol.

In vitro assays such as those described above may be used advantageously to screen rapidly large numbers of selective binding agents. The assays may be automated to screen compounds generated in phage display, synthetic peptide and chemical synthesis libraries.

Selective binding agents may also be screened in cell culture using cells and cell lines expressing either polypeptide. Cells and cell lines may be obtained from any mammal, but preferably will be from human or other primate, canine, or rodent sources. As an example, the binding of receptor and cognate ligand on the cell surface is evaluated in the presence or absence of selective binding agents, with the extent of binding determined by flow cytometry using a biotinylated antibody to the ligand.

The selective binding agents of the inventive subject matter may be employed in any known assay method, such as radioimmunoassays, competitive binding assays, direct and indirect sandwich assays (ELISAs), and immunoprecipitation assays (Sola, Monoclonal Antibodies: A Manual of Techniques, pp. 147-158 (CRC Press, 1987)).

Terms Related to Soluble Protein Agents

The term "half-life extender" refers to a molecule that prevents degradation and/or increases half-life, reduces toxicity, reduces immunogenicity, or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide (e.g., dextran); any natural or synthetic protein, polypeptide or peptide that binds to a salvage receptor; albumin, including human serum albumin (HSA), leucine zipper domain, and other such proteins and protein fragments. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

Antibody-Related Terms

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In preferred embodiments, an antibody is said to specifically bind an antigen when the dissociation constant is less than or equal to about 10 nM, more preferably when the dissociation constant is less than or equal to about 100 pM, and most preferably when the dissociation constant is less than or equal to about 10 pM.

"Antibody" or "antibody peptide(s)" refer to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, immunologically functional immunoglobulin fragments, heavy chain, light chain, and single-chain antibodies.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus.

The term "light chain" includes a full-length light chain and fragments thereof having sufficient variable region sequence to confer binding specificity. A full-length light chain includes a variable region domain, $V_L$, and a constant region domain, $C_L$. Like the heavy chain, the variable region domain of the light chain is at the amino-terminus of the polypeptide.

A "Fab fragment" is comprised of one light chain and the $C_H1$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_H1$ and $C_H2$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference for any purpose.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148:1547-1553.

In assessing antibody binding and specificity according to the invention, an antibody "substantially inhibits" adhesion of an antigen to a binding partner therefor when an excess of antibody reduces the quantity of antigen bound to binding partner by at least about 20%, 40%, 60%, 80%, 85%, or more (as measured in an in vitro competitive binding assay).

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to an antigen, preventing binding of the antigen to a binding partner therefor, interrupting the biological response resulting from binding of the antigen and binding partner, or any combination thereof.

The term "agent" means a chemical compound, a mixture of chemical compounds, a biological macromolecule, or an extract made from biological materials.

DNA and Protein Preparation Terms

Conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, *Molecular Cloning: A Laboratory Manual*, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

The term "isolated polynucleotide" means that the subject polynucleotide, (1) is not associated (covalently or noncovalently) with all or a portion of other polynucleotides with which the subject polynucleotide is associated in nature, (2) is associated with a molecule with which it is not associated in nature, or (3) does not occur in nature associated with any other polynucleotides. Such an isolated polynucleotide may be genomic DNA, cDNA, mRNA or other RNA, of synthetic origin, or any combination thereof.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

The terms "polypeptide" or "protein" means molecules having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass antibodies, or sequences that have deletions from, additions to, and/or substitutions of one or more amino acid of such antibody. The term "polypeptide fragment" refers to a polypeptide that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains. In the case of an antibody, useful fragments include but are not limited to a CDR region, a variable domain of a heavy or light chain, a portion of an antibody chain or just its variable region including two CDRs, and the like.

The terms "naturally occurring" and "native" mean that the biological materials (molecules, sequences, protein complexes, cells, and the like) to which the terms are applied can be found in nature and are not manipulated by man. For example, a polypeptide or polynucleotide sequence that is present in an organism (including viruses) that can be isolated from a source in nature and that has not been intentionally modified by man is naturally occurring. Likewise, the terms "non-naturally occurring" or "non-native" refer to a material that is not found in nature or that has been structurally modified or synthesized by man.

The term "operably linked" means that the components to which the term is applied are in a relationship that allows them to carry out their inherent functions under suitable conditions. For example, a control sequence "operably linked" to a protein coding sequence is ligated thereto so that expression of the protein coding sequence is achieved under conditions compatible with the transcriptional activity of the control sequences.

The term "control sequence" means that the subject polynucleotide sequence can effect expression and processing of coding sequences to which it is ligated. The nature of such control sequences may depend upon the host organism. In particular embodiments, control sequences for prokaryotes may include a promoter, ribosomal binding site, and transcription termination sequence. In other particular embodiments, control sequences for eukaryotes may include promoters comprising one or a plurality of recognition sites for transcription factors, transcription enhancer sequences, and transcription termination sequence. In certain embodiments, "control sequences" can include leader sequences and/or fusion partner sequences.

The term "polynucleotide" means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term includes single and double stranded forms of DNA.

The term "oligonucleotide" means a polynucleotide comprising a length of 200 bases or fewer. In preferred embodiments, oligonucleotides are 10 to 60 bases in length. In more preferred embodiments, oligonucleotides are 12, 13, 14, 15, 16, 17, 18, 19, or 20 to 40 bases in length. Oligonucleotides may be single stranded or double stranded, e.g., for use in the construction of a mutant gene. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups or modified or substituted bases.

The term "oligonucleotide linkages" includes linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. (1986), *Nucl. Acids Res.* 14:9081; Stec et al. (1984), *J. Am. Chem. Soc.* 106:6077; Stein et al. (1988), *Nucl. Acids Res.* 16:3209; Zon et al. (1991), *Anti-Cancer Drug Design* 6:539; Zon et al. (1991), *Oligonucleotides and Analogues: A Practical Approach*, pp. 87-108 (F. Eckstein, ed.), Oxford University Press, Oxford England; Stec et al., U.S. Pat. No. 5,151,510; Uhlmann and Peyman (1990), *Chemical Reviews* 90:543, the disclosures of which are hereby incorporated by reference for any purpose. An oligonucleotide of the invention can include a label, including a radiolabel, a fluorescent label, a hapten or an antigenic label, for detection assays.

The term "vector" means any molecule (e.g., nucleic acid, plasmid, or virus) used to transfer coding information to a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and RNA splicing, if introns are present, of a coding region operably linked thereto.

The term "host cell" means a cell that has been transformed, or is capable of being transformed, with a nucleic acid sequence and thereby expresses a selected gene of interest. The term includes the progeny of the parent cell, whether or not the progeny is identical in morphology or in genetic make-up to the original parent cell, so long as the selected gene is present.

The term "transduction" means the transfer of genes from one bacterium to another, usually by phage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, *Molecular Cloning: A Laboratory Manual, Id.*; Davis et al., 1986, *Basic Methods in Molecular Biology*, Elsevier; and Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA. For example, a cell is transformed where it is genetically modified from its native state by transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The term "identity" refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between sequences of two or more nucleotides or two or more amino acids. "Identity" measures the percentage of identical matches between the smaller of two or more sequences with gap alignments (if any) addressed by a particular mathematical model or computer program (i.e., "algorithms").

The term "similarity" is used in the art with regard to a related concept; in contrast to "identity," however, "similarity" refers to a measure of relatedness that includes both identical matches and conservative substitution matches. If two polypeptide sequences have, for example, 10/20 identical amino acids, and the remainder are all non-conservative substitutions, then the percentage identity and similarity would both be 50%. If in the same example, there are five more positions where there are conservative substitutions, then the percentage identity remains 50%, but the percentage similarity would be 75% (15/20). Therefore, in cases where there are conservative substitutions, the percentage similarity between two polypeptides will be higher than the percentage identity between those two polypeptides.

Identity and similarity of related nucleic acids and polypeptides can be readily calculated by known methods. Such methods include, but are not limited to, those described in *Computational Molecular Biology*, (Lesk, A. M., ed.), 1988, Oxford University Press, New York; Biocomputing: Informatics and Genome Projects, (Smith, D. W., ed.), 1993, Academic Press, New York; *Computer Analysis of Sequence Data*, Part 1, (Griffin, A. M., and Griffin, H. G., eds.), 1994, Humana Press, New Jersey; von Heinje, G., *Sequence Analysis in Molecular Biology*, 1987, Academic Press; *Sequence Analysis Primer*, (Gribskov, M. and Devereux, J., eds.), 1991, M. Stockton Press, New York; Carillo et al., 1988, *SIAM J. Applied Math.* 48:1073; and Durbin et al., 1998, *Biological Sequence Analysis*, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.* 12:387; Genetics Computer Group, University of Wisconsin, Madison, Wis.), BLASTP, BLASTN, and FASTA (Altschul et al., 1990, *J. Mol. Biol.* 215:403-410). The BLASTX program is publicly available from the National Center for Biotechnology Information (NCBI) and other sources (*BLAST Manual*, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percentage sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure* 5:345-352 for the PAM 250 comparison matrix; Henikoff et al., 1992, *Proc. Natl. Acad. Sci USA* 89:10915-10919 for the BLOSUM 62 comparison matrix) is also used by the algorithm.

In certain embodiments, the parameters for a polypeptide sequence comparison include the following:

Algorithm: Needleman et al. (1970), *J. Mol. Biol.* 48:443-453;

Comparison matrix: BLOSUM 62 from Henikoff et al. (1992), supra;

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

The term "naturally occurring," as used to refer to amino acids, refers to the twenty conventional amino acids. See *Immunology—A Synthesis*, 2nd Edition, (E. S. Golub and D. R. Gren, eds.), Sinauer Associates: Sunderland, Mass. (1991), incorporated herein by reference for any purpose. Peptide analogs are commonly used in the pharmaceutical industry as non-peptide drugs with properties analogous to those of the template peptide. These types of non-peptide compounds are termed "peptide mimetics" or "peptidomimetics". See Fauchere (1986), *Adv. Drug Res.* 15:29; Veber & Freidinger, 1985, *TINS p.* 392; and Evans et al. (1987), *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm peptide or polypeptide (i.e., a peptide or polypeptide that has a biochemical property or pharmacological activity), such as human antibody, but have one or more peptide linkages optionally replaced by a linkage selected from: —$CH_2$—NH—, —$CH_2$—S—, —$CH_2$—$CH_2$—, —CH═CH— (cis and trans), —$COCH_2$—, —CH(OH)$CH_2$—, and —$CH_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

The terms "label" or "labeled" refers to incorporation of a detectable marker, e.g., by incorporation of a radiolabeled amino acid or attachment to a polypeptide of biotin moieties that can be detected by marked avidin (e.g., streptavidin preferably comprising a detectable marker such as a fluorescent marker, a chemiluminescent marker or an enzymatic activity that can be detected by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^3$H, $^{14}$C, $^{15}$N, $^{35}$S, $^{90}$Y, $^{99m}$Tc, $^{111}$In, $^{125}$I, $^{131}$I), fluorescent labels (e.g., fluorescein isothiocyanate (FITC), rhodamine, or lanthanide phosphors), enzymatic labels (e.g., horseradish peroxidase, ß-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms (such as $(CH_2)_n$, where n<about 20) of various lengths to reduce potential steric hindrance.

The term "biological sample" includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph, lymph nodes, synovial tissue, chondrocytes, synovial macrophages, endothelial cells, vascular tissue (particularly inflamed vascular tissue), and skin. The terms "pharmaceutical agent" and "drug" refer to a chemical compound or composition capable of inducing a desired therapeutic effect when properly administered to a patient.

The terms "substantially pure" and "substantially purified" mean a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

Amino Acids

The twenty naturally-occurring amino acids and their abbreviations follow conventional usage. See *Immunology—A Synthesis*, 2nd Edition, (E. S. Golub and D. R. Gren, eds.), Sinauer Associates: Sunderland, Mass. (1991), incorporated herein by reference for any purpose. Stereoisomers (e.g., D-amino acids) of the twenty conventional amino acids, unnatural amino acids such as—, -disubstituted amino acids, N-alkyl amino acids, and other unconventional amino acids may also be suitable components for polypeptides of the invention. Examples of unconventional amino acids include: 4-hydroxyproline, -carboxyglutamate, —N,N,N-trimethyllysine, —N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences".

Naturally occurring amino acid residues may be divided into classes based on common side chain properties:
1) hydrophobic: norleucine (Nor or Nle), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced, for example, into regions of a human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyricAcid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Op. in Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, Ann. Rev. Biochem. 47:251-276; and Chou et al., 1979, *Biophys. J.* 26:367-384. Moreover, computer programs are currently available to assist with predicting secondary structure. One method for predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See Holm, 1999, supra; and Brenner, 1997, supra).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, *Structures and Molecular Principles*, (Creighton, ed.), 1984, W. H. Freeman and Company, New York; *Introduction to Protein Structure* (C. Branden and J. Tooze, eds.), 1991, Garland Publishing, New York, N.Y.; and Thornton et al. (1991), *Nature* 354:105, each of which are incorporated herein by reference.

Preparation of Antibodies

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, a "J" region of about 12 or more amino acids joins the variable region and constant regions, with the heavy chain also including a "D" region of about 10 more amino acids. See, e.g., *Fundamental Immunology*, Ch. 7, $2^{nd}$ ed., (Paul, W., ed.), 1989, Raven Press, N.Y. (incorporated by reference in its entirety for all purposes). The combination of the variable regions of each light chain/heavy chain pair typically forms the antigen-binding site.

The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of *Kabat Sequences of Proteins of Immunological Interest* (1987 and 1991, National Institutes of Health, Bethesda, Md.), Chothia & Lesk, 1987, *J. Mol. Biol.* 196:901-917, or Chothia et al., 1989, *Nature* 342:878-883).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, *Nature* 256:495-497) and the human B-cell hybridoma method (Kozbor, 1984, *J. Immunol.* 133:3001; and Brodeur et al., 1987, *Monoclonal Antibody Production Techniques and Applications*, (Marcel Dekker, Inc., New York), pp. 51-63).

Monoclonal antibodies may be modified for use as therapeutics. One example is a "chimeric" antibody in which a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Other examples are fragments of such antibodies, so long as they exhibit the desired biological activity. See, U.S. Pat. No. 4,816,567; and Morrison et al. (1985), *Proc. Natl. Acad. Sci. USA* 81:6851-6855. A related development is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass.

Another development is the "humanized" antibody. Methods for humanizing non-human antibodies are well known in the art. (See U.S. Pat. Nos. 5,585,089, and 5,693,762). Generally, a humanized antibody is produced by a non-human animal, and then certain amino acid residues, typically from non-antigen recognizing portions of the antibody, are modified to be homologous to said residues in a human antibody of corresponding isotype. Humanization can be performed, for example, using methods described in the art (Jones et al., 1986, *Nature* 321:522-525; Riechmann et al., 1988, *Nature* 332:323-327; Verhoeyen et al., 1988, *Science* 239:1534-1536), by substituting at least a portion of a rodent variable region for the corresponding regions of a human antibody.

More recent and more promising is the development of human antibodies without exposure of antigen to human beings ("fully human antibodies"). Using transgenic animals (e.g., mice) that are capable of producing a repertoire of human antibodies in the absence of endogenous mouse immunoglobulin production, such antibodies are produced by immunization with an antigen (typically having at least 6 contiguous amino acids), optionally conjugated to a carrier. See, for example, Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of these methods, transgenic animals are produced by incapacitating the endogenous mouse immunoglobulin loci encoding the mouse heavy and light immunoglobulin chains therein, and inserting loci encoding human heavy and light chain proteins into the genome thereof. Partially modified animals, which have less than the full complement of modifications, are then cross-bred to obtain an animal having all of the desired immune system modifications. When administered an immunogen, these transgenic animals produce antibodies that are immunospecific for these antigens having human (rather than murine) amino acid sequences, including variable regions. See PCT Publication Nos. WO96/33735 and WO94/02602, incorporated by reference. Additional methods are described in U.S. Pat. No. 5,545,807, PCT Publication Nos. WO91/10741, WO90/04036, and in EP 546073B1 and EP 546073A1, incorporated by reference. Human antibodies may also be produced by the expression of recombinant DNA in host cells or by expression in hybridoma cells as described herein.

Fully human antibodies can also be produced from phage-display libraries (as disclosed in Hoogenboom et al., 1991, *J. Mol. Biol.* 227:381; and Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT Publication No. WO99/10494, incorporated by reference, which describes the isolation of high affinity and functional agonistic antibodies for MPL- and msk-receptors using such an approach.

Once the nucleotide sequences encoding such antibodies have been determined, chimeric, CDR-grafted, humanized, and fully human antibodies also may be produced by recombinant methods. Nucleic acids encoding the antibodies are introduced into host cells and expressed using materials and procedures generally known in the art.

The invention provides for use of one or a plurality of monoclonal antibodies. In preferred embodiments, the invention provides nucleotide sequences encoding, and amino acid sequences comprising, heavy and light chain immunoglobulin molecules, particularly sequences corresponding to the variable regions thereof. In preferred embodiments, sequences corresponding to complementarity determining regions (CDR's), specifically from CDR1 through CDR3, are provided. In additional preferred embodiments, the invention provides hybridoma cell lines expressing such immunoglobulin molecules and monoclonal antibodies produced therefrom.

The ability to clone and reconstruct megabase-sized human loci in yeast artificial chromosomes (YACs) and to introduce them into the mouse germline provides an advantageous approach to elucidating the functional components of very large or crudely mapped loci as well as generating useful models of human disease. Furthermore, the utilization of such technology for substitution of mouse loci with their human equivalents provides unique insights into expression and regulation of human gene products during development, their communication with other systems, and their involvement in disease induction and progression.

An important practical application of such a strategy is the "humanization" of the mouse humoral immune system.

Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy provides a source for production of fully human monoclonal antibodies (MAbs), particularly for use as therapeutic agents. Fully human antibodies are expected to minimize the immunogenic and allergic responses intrinsic to mouse or mouse-derivatized Mabs, and to thereby increase the efficacy and safety of administered antibodies in therapeutic applications. Fully human antibodies can be used in the treatment of chronic and recurring human diseases, such as osteoarthritis, rheumatoid arthritis, and other inflammatory conditions, the treatment thereof requiring repeated antibody administration.

One skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

In certain embodiments, the skilled artisan can use constant regions from species other than human along with the human variable region(s) in such mice to produce chimeric antibodies. The antibodies of the invention can be produced by immunizing such animals with full-length antigen or a fragment thereof. See, for example, International Patent Application, Publication WO 93/12227).

The CDRs of the light and heavy chain variable regions of antibodies of the invention can be grafted to framework regions (FRs) from the same, or another, species. In certain embodiments, the CDRs of the light and heavy chain variable regions of antibody may be grafted to consensus human FRs. To create consensus human FRs, FRs from several human heavy chain or light chain amino acid sequences are aligned to identify a consensus amino acid sequence. The FRs of the antibody heavy chain or light chain can be replaced with the FRs from a different heavy chain or light chain. Rare amino acids in the FRs of the heavy and light chains of anti-IL-1R1 antibody typically are not replaced, while the rest of the FR amino acids can be replaced. Rare amino acids are specific amino acids that are in positions in which they are not usually found in FRs. The grafted variable regions from antibodies of the invention can be used with a constant region that is different from the constant region of an antibody of this invention. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

Antibodies of the invention are preferably prepared using transgenic mice that have a substantial portion of the human antibody-producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In preferred embodiments, the skilled worker may employ methods as disclosed in International Patent Application Publication No. WO 98/24893, which is hereby incorporated by reference for any purpose. See also Mendez et al., 1997, *Nature Genetics* 15:146-156, which is hereby incorporated by reference for any purpose.

The monoclonal antibodies (MAbs) and other agents of the invention can be produced by a variety of techniques, including conventional monoclonal antibody methodology, e.g., the standard somatic cell hybridization technique of Kohler and Milstein, 1975, *Nature* 256:495. Although somatic cell hybridization procedures are preferred, in principle, other techniques for producing monoclonal antibodies can be employed, e.g., viral or oncogenic transformation of B-lymphocytes.

In a preferred embodiment, human monoclonal antibodies can be generated using mice referred to as "HuMab" mice, contain a human immunoglobulin gene minilocus that encodes unrearranged human heavy ($\mu$ and $\gamma$) and $\kappa$ light chain immunoglobulin sequences, together with targeted mutations that inactivate the endogenous $\mu$ and $\kappa$ chain loci. Lonberg et al., 1994, *Nature* 368:856-859. Accordingly, the mice exhibit reduced expression of mouse IgM or $\kappa$ and in response to immunization, the introduced human heavy and light chain transgenes undergo class switching and somatic mutation to generate high affinity human IgG $\kappa$ monoclonal antibodies. Lonberg et al., supra; Lonberg and Huszar, 1995, *Intern. Rev. Immunol.* 13:65-93; Harding and Lonberg, 1995, *Ann. N.Y. Acad. Sci.* 764:536-546. The preparation of HuMab mice is described in detail in Taylor et al., 1992, *Nucleic Acids Res.* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg & Huszar, 1995, *Intern. Rev. Immunol.* 13:65-93; Harding & Lonberg, 1995, *Ann. N.Y. Acad. Sci* 764:536-546; Fishwild et al., 1996, *Nature Biotechnology* 14:845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety.

Advantageously, fully human monoclonal antibodies are produced as follows. Transgenic mice containing human immunoglobulin genes are immunized with the antigen of interest. Lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to the antigen of interest is provided.

In preferred embodiments, antibodies of the invention are produced by hybridoma lines. In these embodiments, antibodies of the invention would typically bind to their associated antigen with a dissociation constant ($K_d$) of between approximately 4 pM and 100 pM.

In preferred embodiments, the antibodies of the invention are of the IgG1, IgG2, or IgG4 isotype, with the IgG2 isotype most preferred. In preferred embodiments of the invention, the antibodies comprise a human kappa light chain and a human IgG1, IgG2, or IgG4 heavy chain. In particular embodiments, the variable regions of the antibodies are ligated to a constant region other than the constant region for the IgG1, IgG2, or IgG4 isotype. In certain embodiments, the antibodies of the invention have been cloned for expression in mammalian cells.

In certain embodiments, conservative amino acid substitutions to the heavy and light chains of the antibody (and corresponding modifications to the encoding nucleotides) will produce antibodies having functional and chemical characteristics similar to those of the unsubstituted antibody. In contrast, substantial modifications in the functional and/or chemical characteristics of the antibody may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (Wells, 1991, Methods Enzymol. 202:390 (ed. J. J. Langone), Academic Press, London).

Desired amino acid substitutions (whether conservative or non-conservative) can be determined by those skilled in the art at the time such substitutions are desired. In certain embodiments, amino acid substitutions can be used to identify important residues of the antibody, or to increase or decrease the affinity of the antibodies described herein.

In alternative embodiments, antibodies of the invention can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Such procedures are exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the methods of the invention, a nucleic acid molecule encoding the amino acid sequence of a heavy chain constant region, a heavy chain variable region, a light chain constant region, or a light chain variable region of an antibody of the invention is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, *Meth. Enzymol. Vol.* 185, Academic Press. N.Y.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification or detection of the antibody from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. A neomycin resistance gene may also be used for selection in both prokaryotic and eukaryotic host cells.

Other selectable genes may be used to amplify the gene that will be expressed. Amplification is the process wherein genes that are in greater demand for the production of a protein critical for growth or cell survival are reiterated generally in tandem within the chromosomes of successive generations of recombinant cells. Examples of suitable selectable markers for mammalian cells include dihydrofolate reductase (DHFR) and promoterless thymidine kinase. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene. As a result, increased quantities of a polypeptide can be synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

The expression and cloning vectors of the invention will typically contain a promoter that is recognized by the host organism and operably linked to the molecule encoding the antibody. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding heavy chain or light chain comprising an antibody of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto et al., 1980, *Cell* 22:787-97); the herpes thymidine kinase promoter (Wagner et al., 1981, *Proc. Natl. Acad. Sci. USA* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. USA* 75:3727-31); or the tac promoter (DeBoer et al., 1983, *Proc. Natl. Acad. Sci. USA* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al., 1984, *Cell* 38:647-58; Adames et al., 1985, *Nature* 318:533-38; Alexander et al., 1987, *Mol. Cell. Biol.* 7:1436-44); the mouse mammary tumor virus control region that is active in testicular, breast, lymphoid and mast cells (Leder et al., 1986, *Cell* 45:485-95); the albumin gene control region that is active in liver (Pinkert et al., 1987, *Genes and Devel.* 1:268-76); the alpha-feto-protein gene control region that is active in liver (Krumlauf et al., 1985, *Mol. Cell. Biol.* 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al., 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

An enhancer sequence may be inserted into the vector to increase transcription of DNA encoding light chain or heavy chain comprising an antibody of the invention by higher eukaryotes. Enhancers are cis-acting elements of DNA, usually about 10-300 bp in length, that act on the promoter to increase transcription. Enhancers are relatively orientation- and position-independent. They have been found 5' and 3' to the transcription unit. Several enhancer sequences available from mammalian genes (e.g., globin, elastase, albumin, alpha-feto-protein and insulin) are known. Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain has been inserted into the proper site of the vector, the completed vector may be inserted into a suitable host cell for amplification and/or polypeptide expression. The transformation of an expression vector for an antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes an antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, one may select cell lines by determining which cell lines have high expression levels and produce antibodies with constitutive binding properties. In another embodiment, one may select a cell line from the B cell lineage that does not make its own antibody but has a capacity to make and secrete a heterologous antibody (e.g., mouse myeloma cell lines NS0 and SP2/0).

Preparation of Other Agents

Persons of ordinary skill in the art are able to prepare additional agents, such as soluble fragments of IL-27 receptor and WSX-1, using the techniques described hereinabove. Further in accordance with the present invention, such an agent may be linked to a half-life extender such as a polymer (e.g., PEG or dextran), human serum albumin (HSA), transthyretin (TTR), a leucine zipper domain (LZ) or an Fc domain, which is preferred. The half-life extender and the agent may be linked through the N- or C-terminus of the agent. The preferred half-life extender is an Fc domain, and the preferred Fc domain is an IgG Fc domain.

The term "pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

THE INVENTIVE SUBJECT MATTER

The inventive subject matter relates to methods for modulating an immune response, and pharmaceutical compositions comprising an effective amount of an IL-27R/WSX-1 ligand.

Although recent work has described IL-27 and its receptor, WSX-1, as promoters of Th1 differentiation in naive CD4+ T cells, Applicants have determined that signaling through this receptor is involved in limiting the intensity and duration of T cell activity. When WSX-1-deficient mice are infected with the intracellular pathogen *Toxoplasma gondii*, they establish protective T cell responses, characterized by production of inflammatory cytokines and control of parasite replication. However, infected WSX-1$^{-/-}$ mice are unable to downregulate these protective responses, and develop a lethal, T cell-mediated inflammatory disease. This pathology was characterized by the excessive production of IFN-_, persistence of highly activated T cells, and enhanced T cell proliferation in vivo. Together, these findings demonstrate that WSX-1 is not required for the generation of IFN-γ-mediated immunity to this parasitic infection and identify a novel function for this receptor as a potent antagonist of T cell-mediated, immune hyperactivity.

Contrary to the previous consensus understanding, we have demonstrated that WSX-1-deficient mice infected with *T. gondii* are able to develop a strong Th1 type response and control parasite replication, but are unable to downregulate this protective response and develop a lethal, T cell-mediated inflammatory disease. This pathology was characterized by the excessive production of IFN-γ, persistence of highly activated T cells, and enhanced T cell proliferation in vivo. The phenotype could be recapitulated in vitro as Th1 polarization of WSX-1$^{-/-}$ CD4+ T cells led to increased proliferation and IFN-γ secretion. However, this work also confirmed that, under nonpolarizing conditions, WSX-1 is required for optimal IFN-γ production. Further analysis revealed that exogenous IL-27 can activate STAT1, STAT3, and STAT5: STAT family members that have traditionally been associated with cellular activation but have also recently been linked with the inhibition of immune functions. Together, these findings demonstrate that WSX-1 is not required for the generation of IFN-γ-mediated immunity to *T. gondii* and identify a novel function for WSX-1 as a potent antagonist of T cell-mediated immune hyperactivity.

Given the importance of IL-12 in resistance to intracellular pathogens, experiments were performed to determine the role of IL-27/WSX-1 in immunity to *Toxoplasma gondii*, an obligate intracellular parasite that is an important opportunistic pathogen of prenatal infants and immunocompromised adults. Resistance to this pathogen is characterized by the development of an IL-12-dependent Th1 type response dominated by the production of IFN-γ by CD4+ and CD8+ T cells. A strong, protective response leads to control of parasite replication but a failure to appropriately regulate this response can lead to severe T cell mediated immune-pathology characterized by the overproduction of inflammatory cytokines.

Methods of the Inventive Subject Matter

Based primarily on in vitro experiments that showed the IL-27/WSX-1 receptor-ligand interaction could enhance IFN-γ production, a consensus emerged that WSX-1 was an essential receptor for the development of Th1 type responses. However, the present disclosure demonstrates that under the strongly Th1 polarizing conditions that occur during toxoplasmosis or in vitro culture, WSX-1 is not required for the development of Th1 effector cells. Unexpectedly, through infection of WSX-1-deficient mice with *T. gondii*, we have found a regulatory role for this receptor. WSX-1$^{-/-}$ animals exhibit prolonged IFN-γ responses and an accumulation of highly activated T cells that is associated with increased T cell proliferation.

It is well established that antigen dose and cytokine environment are critical factors in the differentiation of naive CD4+ T cells into effector Th1 and Th2 cells. Moreover, T cells must proliferate, not only to acquire effector functions, but also to curb activation and thereby limit the duration and intensity of an immune response.

Figures 6A, 6B:
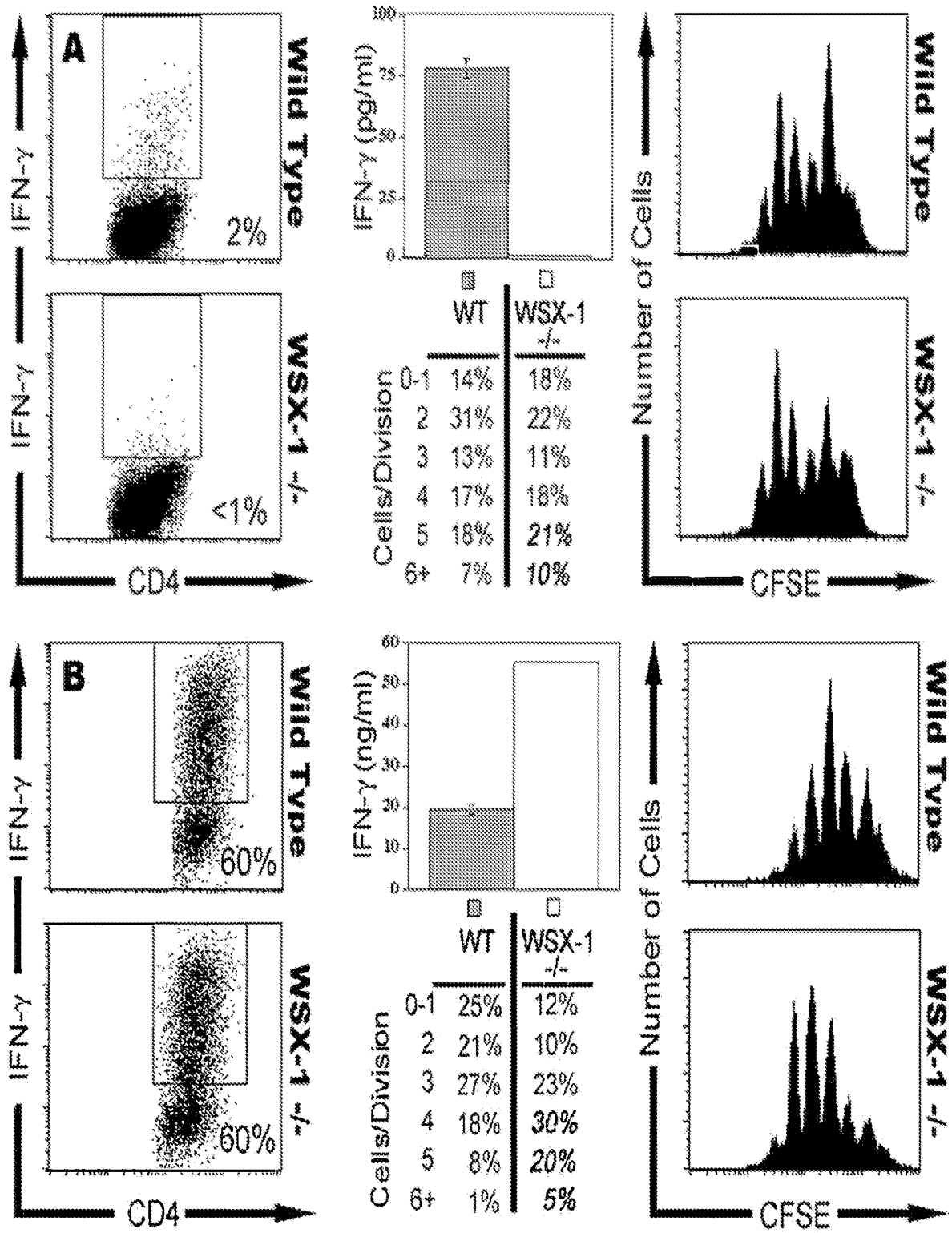
FIG. 6A is a flow cytometry photograph and two graphs which depict naive CD4$^+$ T cells purified from uninfected wild type or WSX-1$^{-/-}$ spleens, stained with CFSE, and activated with soluble αCD3 under nonpolarizing conditions.
FIG. 6B is a flow cytometry photograph and two graphs which depict naive CD4+ T cells purified from uninfected wild type or WSX-1$^{-/-}$ spleens, stained with CFSE, and activated with Th1 soluble αCD3 under polarizing conditions.

Because the role of IL-27/WSX-1 in T cell differentiation was previously assessed using ConA in combination with polarizing cytokines, it is possible that the enhanced proliferation of these cells led to abbreviated cytokine production, which could then be interpreted as a defect in Th1 differentiation. We show here that when T cells are activated through TCR ligation and in highly polarizing conditions, there is an important role for IL-27/WSX-1 as a negative regulator of Th1 type responses. These finding are consistent with a recent report in which CD4+ T cells from mice lacking the EBI3 component of IL-27 produced significantly more IFN-γ than their wild-type counterparts in vitro. While it is clear that WSX-1 CD4f T cells do not have an intrinsic defect in their ability to become Th1 effector cells, it has been reported that recombinant IL-27 can synergize with IL-12 to enhance IFN-γ production by naive T cells and NK cells. Therefore, the ability of IL-27 to activate STAT-1 and thereby induce expression of T-bet, a key transcription factor in Th1 differentiation, may be crucial for maximal Th1 differentiation when concentrations of polarizing cytokine are limiting (FIG. 6A). However, in the context of high IL-12 concentrations, like those induced by acute toxoplasmosis, there is no requirement for IL-27-induced expression of T-bet, thus confirming a central role for IL-12, and not IL-27, in the development of IFN-γ responses that are essential for control of *T. gondii*.

During infection, the ability to downregulate T cell responses after pathogen control is a critical function of an appropriate immune response, but little was known about the mechanisms that mediate this process. In our work, STAT4 phosphorylation could not be detected after treatment of naive cells with either IL-12 or IL-27. Though the absence of functional IL-12R on the surface of naive CD4+ T cells explains the relative inactivity of IL-12 in this assay, a recent report on WSX-1 signaling in naive human lymphocytes suggests that despite functional receptor expression, IL-27 fails to activate STAT4. Furthermore, this finding is consistent with previous work that indicate that exogenous IL-27 does not lead to STAT4 phosphorylation in WSX-1 transfected murine cell lines. Nevertheless, the recognition that WSX-1 can activate STAT1, STAT3, and STAT5 does provide an insight into the pathways that are involved in the negative regulation of T cell responses. While tyrosine phosphorylation of these STAT family members has been previously associated with the activation of immune cells, it is becoming clear that they also have a crucial role in preventing immune hyperactivity. Cytokines like IFN-γ, IFN-α/β, and IL-6 activate similar STAT pathways and can have profound suppressive effects on immune responses. Although little is known about the molecular mechanisms governing these inhibitory processes, several studies have shown that STAT1 is a negative regulator of proliferation and IFN-γ production by Th1 cells. Additionally, ablation of STAT3 in bone marrow haematopoetic progenitors led to the development of immune-mediated colitis in mice, while germline deletion of the STAT3β isoform results in impaired recovery from LPS-induced shock. Thus, the absence of IL-27-mediated STAT activation could provide a molecular mechanism for the T cell hyperactivity observed in WSX- 1<sup>−/−</sup> mice that have been infected with *T. gondii*. However, it is still uncertain whether WSX-1-dependent STAT activation can directly inhibit T cell responses or operates through other trans factors, such as SOCS family members to limit the ability of effector T cells to respond to growth and survival stimuli. Although SOCS1-deficient mice spontaneously develop severe liver pathology similar that of WSX-1$^{-/-}$ mice infected with *T. gondii*, initial work has not revealed decreased, in vitro expression of SOCS1 by WSX-1$^{-/-}$ T cells.

A role for WSX-1 in the downregulation of T cell responses does not appear to be restricted to toxoplasmosis as infection of WSX-1$^{-/-}$ mice with *Trypanosoma cruzi* also resulted in the development of immune pathology. Other work has also found that when WSX-1$^{-/-}$ mice were infected with the intestinal helminth *Trichuris muris*, they developed an exaggerated Th2 response that was associated with enhanced expulsion of the parasite (unpublished data). Consequently, the previous report of increased susceptibility of WSX-1$^{-/-}$ mice to *L. major* cannot simply be attributed to a failure in the generation of Th1 responses. Because resistant mouse strains produce an acute Th2 response when challenged with *L. major*, an inability to regulate this acute IL-4 production, in combination with the absence of WSX-1-dependent STAT-1 activation, could inhibit initial generation of protective Th1 type cells and thereby delay disease resolution in WSX-1$^{-/-}$ mice. In support of this hypothesis, in vivo neutralization of IL-4 was found to restore the ability of WSX-1$^{-/-}$ mice to control *L. major* and, in these experiments, WSX-1$^{-/-}$ T cells were found to produce more IFN-γ than those of similarly treated wild type mice (unpublished data).

Together, this work indicates that one role of WSX-1 is to control the kinetics, but not polarity, of an immune response and that signaling through this receptor may act as a general negative regulator of infection-induced T cell effector functions. Consequently, our determination of a role for WSX-1 in the suppression of T cell hyperactivity has immediate clinical implications for T cell-mediated inflammatory disorders and represents a novel target for immune based therapies.

To further demonstrate the importance of IL-27/WSX-1 interactions in modulating immune responses, we have shown the development of a T helper (Th) 2 type immunity response of WSX-1$^{-/-}$ mice infected with the gut dwelling helminth *Trichuris muris*. In contrast to wild type mice the WSX-1$^{-/-}$ mice displayed increased production of Th2 cytokines, elevated intestinal goblet cell and mast cell responses, and accelerated expulsion of *T. muris*. In addition, mast cells were also shown to express WSX-1 and in a model of IgE-mediated mast cell dependent anaphylaxis WSX-1-mice displayed increased changes in vascular permeability. Importantly, the accelerated parasite-induced Th2 responses in WSX-1$^{-/-}$ mice did not appear to be due to an intrinsic defect in IFN-γ production since the blockade of Th1 responses in wild type mice did not result in enhanced Th2 responses or resistance to *T. muris*. Moreover, in vitro assays revealed that naive WSX-1$^{-/-}$ CD4$^{+}$ T cells stimulated under Th2 polarizing conditions displayed enhanced proliferation and secreted elevated levels of IL-5 and IL-13 compared to wild type cells and exogenous IL-27 was shown to suppress the production of IL-4 by wild type CD4$^{+}$ T cells.

As discussed above, the initial consensus that IL-27/WSX-1 was required for optimal Th1 type responses led to the hypothesis that WSX-1$^{-/-}$ mice would be more resistant to *T. muris* as a consequence of reduced IFN-γ responses. Indeed, the finding that WSX-1$^{-/-}$ mice displayed enhanced resistance to *T. muris* supported this hypothesis. However, since WSX-1$^{-/-}$ mice did not appear to have an early defect in IFN-γ production, and the finding that blockade of Th1 responses in wild type mice did not result in enhanced resistance suggested IL-27/WSX-1 signaling was involved in the inhibition of Th2 responses. Moreover, under Th2 polarizing conditions in vitro, WSX-1$^{-/-}$ CD4$^{+}$ T cells displayed enhanced production of Th2 cytokines whereas IL-27 could downregulate the production of IL-4 by wild type CD4$^{+}$ T cells, supporting a direct role for IL-27/WSX-1 as a negative regulator of Th2 cell responses.

While previous work has shown that the IL-27/WSX-1 interaction can promote the production of IFN-γ under non-polarizing conditions, the results presented here identify a role for IL-27/WSX-1 in regulating the development of Th2 responses in vitro and in vivo. These data are in accord with studies in a variety of experimental systems that demonstrated enhanced Th2 type responses in the absence of IL-27/WSX-1 signaling. In addition, recent studies have shown that IL-27 can downregulate the levels of mRNA for GATA3, a transcription factor critical for the development of Th2 responses but whether this is a direct effect of IL-27 or a secondary consequence of other inhibitory effects remains unclear. In some of these experimental systems these effects have previously been attributed to reduced IFN-γ responses, but the data presented here prompt a reappraisal of the role of IL-27/WSX-1 in the regulation of type 2 immunity. For instance, the enhanced susceptibility of WSX-1$^{-/-}$ mice to *Leishmania major* infection may not be due solely to a defect in IFN-γ production as previously reported, but may also be the result of enhanced Th2 cytokine responses in the absence of WSX-1. Supporting this hypothesis, in vivo depletion of IL-4 in WSX-1$^{-/-}$ mice infected with *L. major* restored IFN-γ production and protective immunity.

While most work to date on IL-27/WSX-1 have focused on the role of this cytokine/receptor interaction in the regulation of lymphocyte functions the finding that mast cells can express high levels of WSX-1 and can respond to IL-27 was unexpected. However, it is now becoming clear that other cell types express functional IL-27R; it has been reported that macrophages, dendritic cells, as well as mast cells express this receptor and that primary human mast cells can activate and STAT3 in response to IL-27. The finding that in the absence of WSX-1 mast cell responses are enhanced in a model of passive cutaneous anaphylaxis demonstrates that the IL-27/WSX-1 interaction may provide a general mechanism to downregulate immune activity in multiple cell types. While our data indicates a direct role for IL-27/WSX-1 in the inhibition of Th2 responses, previous studies have demonstrated that the ability of mast cells to produce IL-4 contributes to the development of infection-induced Th2 responses.

The findings that WSX-1$^{-/-}$ mice develop immune-mediated chronic inflammation when infected with *T. gondii* or *T. cruzi*, two parasites that induce strong type 1 immunity, in combination with other work disclosed herein, support the idea that IL-27/WSX-1 has inhibitory effects on pathogen-induced Th1 and Th2 type responses. Thus, it appears that IL-27/WSX-1 signaling can deliver a negative regulatory signal to activated CD4$^{+}$ T cells and thereby limit T cell responses. Such enhanced proliferative responses of WSX-1$^{-/-}$ T cells may be a function of enhanced cell survival, accelerated cell cycle progression, or increased sensitivity to growth factors like IL-2. However, our studies have found that IL-27 does not inhibit T cell proliferation, and the basis for the difference between the enhanced proliferative responses of WSX-1$^{-/-}$ T cells and the effects of rIL-27 are unclear. Without being bound to any particular theory of mode of activity, a possible explanation may be that the different IL-27R components mediate different functional activities or that there is an additional ligand for WSX-1 that is involved in the regulation of T cell proliferation. The identification of a role for the IL-27/WSX-1 interaction in the suppression of in vivo Th2 responses demonstrates that this pathway represents a viable therapeutic target for the treatment of a number of inflammatory conditions associated with aberrant Th2 cytokine production, including asthma, allergy, and autoimmunity.

Taken together, these studies demonstrate a further, novel role for IL-27/WSX-1, in limiting different elements associated with innate and adaptive components of Th2 type responses. Thus, we have shown that the IL-27/WSX-1 interaction is additionally a target for the treatment of inflammatory conditions associated with Th2 type responses.

Thus, the inventive subject matter relates to a method for modulating an immune response in an animal in need thereof, which comprises administering to said animal an effective amount of an IL-27R/WSX-1 ligand.

In another aspect, said modulation is suppression and said ligand is an IL-27R/WSX-1 agonist.

In another aspect, said agonist is selected from the group consisting of IL-27, an active fragment of IL-27, and an agonistic antibody to IL-27R/WSX-1 which enhances IL-27R/WSX-1 activity.

In another aspect, said modulation is activation and said ligand is an IL-27R/WSX-1 antagonist.

In another aspect, wherein said antagonist is an inactive IL-27 fragment which retains IL-27R/WSX-1 binding affinity, or an antagonist antibody to IL-27R/WSX-1 which suppresses IL-27R/WSX-1 activity.

The inventive subject matter further relates to a method for modulating a T-helper cell mediated immune response in an animal in need thereof, which comprises administering to said animal an effective amount of an IL-27R/WSX-1 ligand.

In another aspect, said modulation is suppression and said ligand is an IL-27R/WSX-1 agonist.

In another aspect, said agonist is selected from the group consisting of IL-27, an active fragment of IL-27, and an agonistic antibody to IL-27R/WSX-1 which enhances IL-27R/WSX-1 activity.

In another aspect, said modulation is activation and said ligand is an IL-27R/WSX-1 antagonist.

In another aspect, said antagonist is an inactive IL-27 fragment which retains IL-27R/WSX-1 binding affinity, or an antagonist antibody to IL-27R/WSX-1 which suppresses IL-27R/WSX-1 activity.

In another aspect, said T-helper cell is Th1.

In another aspect, said T-helper cell is Th2.

The inventive subject matter further relates to a method for modulating an interferon-γ mediated immune response in an animal in need thereof, which comprises administering to said animal an effective amount of an IL-27R/WSX-1 ligand.

In another aspect, said modulation is suppression and said ligand is an IL-27R/WSX-1 agonist.

In another aspect, said agonist is selected from the group consisting of IL-27, an active fragment of IL-27, and an agonistic antibody to IL-27R/WSX-1 which enhances IL-27R/WSX-1 activity.

In another aspect, said modulation is activation and said ligand is an IL-27R/WSX-1 antagonist.

In another aspect, said antagonist is an inactive IL-27 fragment which retains IL-27R/WSX-1 binding affinity, or an antagonist antibody to IL-27R/WSX-1 which suppresses IL-27R/WSX-1 activity.

The inventive subject matter further relates to a method for treating immune hyperactivity in an animal in need thereof, which comprises administering to said animal an effective amount of an IL-27R/WSX-1 ligand.

The inventive subject matter further relates to a method for treating an immune hyperactivity disorder in an animal in need thereof, which comprises administering to said animal an effective amount of an IL-27R/WSX-1 ligand.

In another aspect, said immune disorder is selected from the group consisting of autoimmune disorders, hypersensitivity disorders, allergies, and asthma.

In another aspect, said immune disorder is selected from the group consisting of Acquired Immune Deficiency Syndrome; acute pancreatitis; Addison's disease; alcohol-induced liver injury including alcoholic cirrhosis; Alzheimer's disease; amyelolateroschlerosis; asthma and other pulmonary diseases; atherosclerosis; autoimmune vasculitis; autoimmune hepatitis-induced hepatic injury; biliary cirrhosis; cachexia/anorexia, including AIDS-induced cachexia; cancer, such as multiple myeloma and myelogenous and other leukemias, as well as tumor metastasis; chronic fatigue syndrome; *Clostridium* associated illnesses, including *Clostridium*-associated diarrhea; coronary conditions and indications, including congestive heart failure, coronary restenosis, myocardial infarction, myocardial dysfunction, and coronary artery bypass graft; diabetes, including juvenile onset Type 1, diabetes mellitus, and insulin resistance; endometriosis, endometritis, and related conditions; epididymitis; erythropoietin resistance; fever; fibromyalgia or analgesia; glomerulonephritis; graft versus host disease/transplant rejection; Graves' disease; Guillain-Barre syndrome; Hashimoto's disease; hemolytic anemia; hemorrhagic shock; hyperalgesia; inflammatory bowel diseases including ulcerative colitis and Crohn's disease; inflammatory conditions of a joint and rheumatic diseases including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced arthritis, Sjögren's syndrome, rheumatic fever, polychondritis and polymyalgia rheumatica and giant cell arteritis; inflammatory eye disease, as may be associated with, for example, corneal transplant; inflammatory eye disease, as may be associated with, e.g., corneal transplant; inflammatory bowel disease; ischemia, including cerebral ischemia; Kawasaki's disease; learning impairment; lung diseases; lupus nephritis; multiple sclerosis; myasthenia gravis; myopathiesneuroinflammatory diseases; neurotoxicity; ocular diseases and conditions, including ocular degeneration and uveitis; osteoporosis; pain, including cancer-related pain; Parkinson's disease; pemphigus; periodontal disease; *Pityriasis rubra* pilaris; pre-term labor; prostatitis and related conditions; psoriasis and related conditions; psoriatic arthritis; pulmonary fibrosis; reperfusion injury; rheumatic fever; rheumatoid arthritis; sarcoidosis; scleroderma; septic shock; side effects from radiation therapy; Sjögren's syndrome; sleep disturbance; spondyloarthropathies; systemic lupus erythematosus; temporal mandibular joint disease; thyroiditis; tissue transplantation or an inflammatory condition resulting from strain, sprain, cartilage damage, trauma, and orthopedic surgery; transplant rejection; uveitis; vasculitis; or an inflammatory condition resulting from strain, sprain, cartilage damage, trauma, orthopedic surgery, infection or other disease processes.

The inventive subject matter further relates to a method for treating a T-helper cell mediated disorder in an animal in need thereof, which comprises administering to said animal an effective amount of an IL-27R/WSX-1 ligand.

In another aspect, said T-helper cell mediated disorder is selected from the group consisting of Acquired Immune Deficiency Syndrome; acute pancreatitis; Addison's disease; alcohol-induced liver injury including alcoholic cirrhosis; Alzheimer's disease; amyelolateroschlerosis; asthma and other pulmonary diseases; atherosclerosis; autoimmune vasculitis; autoimmune hepatitis-induced hepatic injury; biliary cirrhosis; cachexia/anorexia, including AIDS-induced cachexia; cancer, such as multiple myeloma and myelogenous and other leukemias, as well as tumor metastasis; chronic fatigue syndrome; *Clostridium* associated illnesses, including *Clostridium*-associated diarrhea; coronary conditions and indications, including congestive heart failure, coronary restenosis, myocardial infarction, myocardial dysfunction, and coronary artery bypass graft; diabetes, including juvenile onset Type 1, diabetes mellitus, and insulin resistance; endometriosis, endometritis, and related conditions; epididymitis; erythropoietin resistance; fever; fibromyalgia or analgesia; glomerulonephritis; graft versus host disease/transplant rejection; Graves' disease; Guillain-Barre syndrome; Hashimoto's disease; hemolytic anemia; hemorrhagic shock; hyperalgesia; inflammatory bowel diseases including ulcerative colitis and Crohn's disease; inflammatory conditions of a joint and rheumatic diseases including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced arthritis, Sjögren's syndrome, rheumatic fever, polychondritis and polymyalgia rheumatica and giant cell arteritis; inflammatory eye disease, as may be associated with, for example, corneal transplant; inflammatory eye disease, as may be associated with, e.g., corneal transplant; inflammatory bowel disease; ischemia, including cerebral ischemia; Kawasaki's disease; learning impairment; lung diseases; lupus nephritis; multiple sclerosis; myasthenia gravis; myopathiesneuroinflammatory diseases; neurotoxicity; ocular diseases and conditions, including ocular degeneration and uveitis; osteoporosis; pain, including cancer-related pain; Parkinson's disease; pemphigus; periodontal disease; *Pityriasis rubra* pilaris; pre-term labor; prostatitis and related conditions; psoriasis and related conditions; psoriatic arthritis; pulmonary fibrosis; reperfusion injury; rheumatic fever; rheumatoid arthritis; sarcoidosis; scleroderma; septic shock; side effects from radiation therapy; Sjogren's syndrome; sleep disturbance; spondyloarthropathies; systemic lupus erythematosus; temporal mandibular joint disease; thyroiditis; tissue transplantation or an inflammatory condition resulting from strain, sprain, cartilage damage, trauma, and orthopedic surgery; transplant rejection; uveitis; vasculitis; or an inflammatory condition resulting from strain, sprain, cartilage damage, trauma, orthopedic surgery, infection or other disease processes.

The inventive subject matter further relates to a method for modulating a T-helper cell mediated immune response in an animal in need thereof, which comprises administering to said animal an effective amount of an IL-27R/WSX-1 ligand.

In another aspect, said T-helper cell is Th1.

In another aspect, said T-helper cell is Th2.

The inventive subject matter further relates to a method of treating immune hyperreactivity, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of suppressing polarized T cells, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating Th1-mediated disease, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating Th2-mediated disease, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating IFN-mediated disease, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating IgE-mediated disease, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating asthma, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

The inventive subject matter further relates to a method of treating allergy, which comprises administering an effective amount of an agent that increases WSX-1 activity.

In another aspect, the agent comprises IL-27 or an active fragment thereof.

In another aspect, the agent comprises an agonistic antibody that binds to an epitope on WSX-1.

In another aspect, the agent comprises an agonistic antibody that binds to an epitope on IL-27R.

In another aspect, the agent comprises an agonistic antibody that binds to an epitope on IL-27RPP.

Inventive Pharmaceutical Compositions

The inventive subject matter also relates to a pharmaceutical composition comprising:
  (i) an effective amount of a compound of formula I . . . ; and
  (ii) a pharmaceutically acceptable carrier.

In another aspect, A pharmaceutical composition comprising:
  (i) an effective amount of an IL-27R/WSX-1 ligand; and
  (ii) a pharmaceutically acceptable carrier.

The novel pharmaceutical compositions of the invention include a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the inventive subject matter.

The compounds of the invention are preferably delivered to the patient by means of a pharmaceutically acceptable carrier. Such carriers are well known in the art and generally will be in either solid or liquid form. Solid form pharmaceutical preparations which may be prepared according to the inventive subject matter include powders, tablets, dispersible granules, capsules, cachets and suppositories. In general, solid form preparations will comprise from about 5% to about 90% by weight of the active agent.

In preferred embodiments, the invention also provides pharmaceutical compositions comprising a therapeutically effective amount of one or a plurality of the antibodies or other agents of the invention together with a pharmaceutically acceptable diluent, carrier, solubilizer, emulsifier, preservative and/or adjuvant. Preferably, acceptable formulation materials are nontoxic to recipients at the dosages and concentrations employed. In preferred embodiments, pharmaceutical compositions comprising a therapeutically effective amount of anti-IL-1R1 antibodies are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide);

solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, trimethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, *Remington's Pharmaceutical Sciences,* 18th Edition, (A. R. Gennaro, ed.), 1990, Mack Publishing Company.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the invention may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, compositions may be prepared for storage by mixing the selected composition having the desired degree of purity with optional formulation agents ("Remington's Pharmaceutical Sciences", 18th ed. (1990, Mack Publishing Co., Easton, Pa. 18042)) in the form of a lyophilized cake or an aqueous solution. Further, in certain embodiments, the product may be formulated as a lyophilizate using appropriate excipients such as sucrose.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the invention may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the invention include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the invention include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

Combination Therapy

It is not expected that compounds of the inventive subject matter will display significant adverse interactions with other synthetic or naturally occurring substances. Thus, a compound of the inventive subject matter may be administered in combination with other compounds and compositions useful for modulating an immune response. In particular the compounds of the inventive subject matter may be administered in combination with other compounds of the inventive subject matter; other immunomodulating substances; etc.

Therapeutic agents of the inventive subject matter can be administered alone or in combination with other therapeutic agents to prevent or to treat various diseases, disorders, and conditions, such as inflammatory or autoimmune diseases. Depending on the disease, disorder or condition and the desired level of treatment, two, three, or more agents may be administered. These agents may be provided together by inclusion in the same formulation or inclusion in a treatment kit, or they may be provided separately. When administered by gene therapy, the genes encoding the protein agents may be included in the same vector, optionally under the control of the same promoter region, or in separate vectors. Particularly preferred molecules in the aforementioned classes are as follows:

- IL-1 inhibitors: IL-1ra proteins and soluble IL-1 receptors. The most preferred IL-1 inhibitor is anakinra.
- TNF-α inhibitors: soluble tumor necrosis factor receptor type I (sTNF-RI; -RI is also called the p55 receptor); soluble tumor necrosis factor receptor type II (also called the p75 receptor); and monoclonal antibodies that bind the TNF receptor. Most preferred is sTNF-RI as described in WO 98/24463, etanercept (Enbrel®), and Avakine®. Exemplary TNF-inhibitors are described in EP 422 339, EP 308 378, EP 393 438, EP 398 327, and EP 418 014.
- Serine protease inhibitors: SLPI, ALP, MPI, HUSI-I, BMI, and CUSI. These inhibitors also may be viewed as exemplary LPS modulators, as SLPI has been shown to inhibit LPS responses. Jin et al. (1997), Cell 88(3): 417-26 (incorporated by reference).

In certain embodiments, the optimal pharmaceutical formulations will be determined by one skilled in the art depending upon considerations such as, for example, the intended route of administration, delivery format, and desired dosage. See, for example, *Remington's Pharmaceutical Sciences*, supra, pp. 1435-1712, the disclosure of which is hereby incorporated by reference. In certain embodiments, such compositions may influence the physical state, stability, rate of in vivo release, and rate of in vivo clearance of the inventive therapeutic agents.

Synthesis of Compounds of the Invention

The inventive compositions may be readily prepared by standard techniques of molecular biology, utilizing techniques known to those of ordinary skill in the art and as described in greater detail herein.

The products and intermediates may be isolated or purified using one or more standard purification techniques known to one of ordinary skill in the art, including, for example, one or more of simple solvent evaporation, recrystallization, distillation, sublimation, filtration, polymerase chain reaction, Southern blotting, Northern blotting, Western blotting, chromatography, including thin-layer chromatography, affinity chromatography, gel filtration chromatography, ion exchange chromatography, FPLC, HPLC (e.g. reverse phase HPLC), column chromatography, flash chromatography, radial chromatography, trituration, salt precipitation, two-phase separation, polymer precipitation, heat denaturation, isoelectric separation, dialysis, and the like.

It is contemplated that suitable IL-27R/WSX-1 ligands may optionally be synthesized as small molecule chemical compounds. Such inventive compounds may be readily prepared by standard techniques of organic chemistry. In the preparation of such small molecule compounds, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the inventive subject matter.

The product and intermediates of chemical synthesis may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

Route(s) of Administration

The route(s) of administration of the compounds and compositions of the inventive subject matter are well known to those skilled in the art (see, for example, "Remington's Pharmaceutical Sciences", supra). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intraarterial, intramuscular, intraperitoneally, intrathecally, intralesional, intraportal, intraventricularly, intrasternal, intra-ocular, intracerebroventricular, intracerebral (intra-parenchymal), and intracranial injection or infusion techniques; by sustained release systems or by implantation devices. In certain embodiments, the compositions may be administered by bolus injection or continuously by infusion, or by implantation device.

To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in on aspect of the inventive subject matter, the compounds and compositions may be administered orally in the form of capsules, tablets, aqueous suspensions, or solutions. Agents that are administered in this fashion can be formulated with or without carriers customarily used in the compounding of solid dosage forms such as tablets and capsules. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. In certain embodiments, a capsule may be designed to release the active portion of the formulation at the point in the gastrointestinal tract when bioavailability is maximized and pre-systemic degradation is minimized. Additional substituents can be included to facilitate absorption of the agent of this invention.

A pharmaceutical composition of the invention is preferably provided to comprise an effective quantity of one or a plurality of the agents of this invention in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical compositions of the invention can be selected for parenteral delivery. The compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired agent in a pharmaceutically acceptable vehicle. A particularly suitable vehicle for parenteral injection is sterile distilled water in which the anti-IL-1R1 antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, agents are formulated as a dry powder for inhalation. In preferred embodiments, inhalation solutions may also be formulated with a propellant for aerosol delivery. In certain embodiments, solutions may be nebulized. Pulmonary administration and formulation methods therefore are further described in International Patent Publication No. WO94/20069, incorporated by reference, which describes pulmonary delivery of chemically modified proteins.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

Additional pharmaceutical compositions will be evident to those skilled in the art, including formulations involving agents of this invention in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, International Patent Publication No. WO93/15722, incorporated by reference, which describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481), copolymers of *L*-glutamic acid and gamma ethyl-L-glutamate (Sidman et al., 1983, *Biopolymers* 22:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use pharmaceutical compositions according to the invention ex vivo. In such instances, cells, tissues or organs that have been removed from the patient are exposed to pharmaceutical compositions after which the cells, tissues and/or organs are subsequently implanted back into the patient.

In particular, agents of this invention can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The effective amount of a pharmaceutical composition to be employed therapeutically will depend, for example, upon the therapeutic context and objectives. One skilled in the art will appreciate that the appropriate dosage levels for treatment will vary depending, in part, upon the molecule delivered, the indication for which the agent of this invention is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 g/kg to up to about 100 mg/kg or more, depending on the factors mentioned above. In preferred embodiments, the dosage may range from 0.1 g/kg up to about 100 mg/kg; more preferably from 1 g/kg up to about 100 mg/kg; or even more preferably from 5 g/kg up to about 100 mg/kg.

Dosing frequency will depend upon the pharmacokinetic parameters of the particular agent in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the inventive subject matter and are not intended to be limitations thereon. Unless otherwise indicated, all percentages are based upon 100% by weight of the final composition.

GENERAL EXPERIMENTAL PROCEDURES

Experimental Animals. Four- to six-week-old wild type, C57B/6 mice, used as controls, were purchased from a commercial supplier. WSX-1$^{-/-}$ mice were bred and maintained as homozygotes in a specific-pathogen free environment. Four- to six-week-old IL-12p40$^{-/-}$ and RAG-2$^{-/-}$ mice were purchased from a commercial supplier and IL-10$^{-/-}$ mice were bred in-house. Mice deficient in IFN-γ were purchased from a commercial supplier. All animals were maintained under specific pathogen free conditions, in accordance to institutional guidelines. In all experiments, mice were infected at five-eight weeks of age, and experimental groups contained three-five animals.

*Toxoplasma gondii* Infections. The ME49 strain of *T. gondii* was maintained in Swiss Webster and CBA/CaJ mice. ME49 bradyzoite cysts were prepared from donor mice as described previously (Cai et al., 2000). Mice were challenged with 20 *T. gondii* cysts either by i.p. or oral administration. Throughout the manuscript, all infections were performed i.p. unless otherwise noted. To assess parasite burden, mice were infected i.p. with *T. gondii* and, after 7 days, peritoneal lavage was performed. Cells were collected for cytospin preparation and the number of infected cells estimated by microscopy (n=3 per group and at least 500 cells counted per mouse). For histological examinations, lungs, heart, spleen, and liver were collected from animals that were infected with *T. gondii* for 0 (uninfected) or 12 days. Organs were fixed in 10% formalin, embedded in paraffin, sectioned, and stained with hematoxylin and eosin. For in vivo depletion of T cells, WSX-1$^{-/-}$ mice were treated with the indicated antibody at days 7, 8, and 9 postinfection. Endotoxin free αCD4 (GK1.5) and αCD8 (H35-17.2) mAbs were grown from hybridomas.

*T. muris* Infection and Antigen. *T. muris* was maintained in genetically susceptible or immunocompromised animals. Between days 35-42 post-infection, adult worms were isolated and cultured in RPMI containing 500 U/ml penicillin and 500 g/ml streptomycin for 24 hours. *T. muris* excretory-secretory Ag was isolated at 4 hours and 24 hours, dialyzed, sterile filtered, and protein concentrations determined by Bradford Assay. Antigen preparations were used in lymphocyte restimulations, 50 g/ml. Deposited eggs were collected after 24 hours of culture, washed three times in sterile water, incubated at room temperature for six weeks, and stored at 4 C. Mice were infected on day zero with 150-200 embryonated eggs and worm burdens assessed on various days post-infection.

Detection of IL-27 and WSX-1 mRNA Levels. IL-27 and WSX-1 levels were determined by RT-PCR. For ex vivo analysis of mRNA expression following *T. gondii* infection, whole splenocytes were isolated from wild type mice that had been infected for 0 (uninfected) and 7 days. For ex vivo analysis of mRNA expression following *T. muris* infection, mRNA was isolated from whole mesenteric lymph node (hereinafter "MLN") cell suspensions using Trizol. After using standard procedures known in the art for isolating mRNA, PCR was utilized for 34 cycles: 95EC, 30 seconds/60EC 30 seconds/72EC 1 minute, to quantify message levels. ß-actin expression was used as an internal control to assure equal loading of every reaction. Primers specific for IL-27p28 (two 20-mers), EBI3 (one 20-mer and one 23-mer), and WSX-1 (two 20-mers) were used. Specific sequences are found in Applicants' publication, Villarino, et al., The IL-27R (WSX-1) Is Required to Suppress T Cell Hyperactivity during Infection, Immunity, 19:645-655 (2003), which is incorporated by reference in its entirety.

Isolation and Culture of Splenocytes for ex vivo Recall Assays. Spleens from infected/uninfected wild type and WSX-1$^{-/-}$ mice were harvested, dissociated into a single cell suspension, and depleted of erythrocytes using 0.86% (wt/vol) ammonium chloride (Sigma). Cells were washed three times and resuspended in complete RPMI 1640 (10% heat-inactivated fetal bovine serum, 100 U/ml penicillin, 1 mg/ml streptomycin, nonessential amino acids, and ß-mercaptoethanol) before being plated at a cell density of $2 \times 10^5$ cells per well in a final volume of 200 µl in 96-well plates (Costar). Where indicated, cells were stimulated with plate bound αCD3 antibody (1 µg/ml) or cultured with soluble *Toxoplasma* antigen (stag, pg/ml). For flow cytometry experiments, cells were cultured at a final density of $2 \times 10^6$ cells/well in a final volume of 1 ml in 24-well plates (Costar).

Cytokine Production Analyses. Levels of IL-12, IFN-γ, IL-10, TNF-α, IL-23, and IL-2 were measured by ELISA. For both splenocyte recall assays and in vitro differentiation assays, supernatants were collected after 72 hr of culture. For detection of intracellular IFN-γ by flow cytometry, all cells were treated with brefeldin A (BFA, 10 µg/ml) for 2 hr prior to fixation and permeabilization with saponin. Cytokine was detected using APC-conjugated_IFN-γ mAb (BD Pharmingen) in combination with surface staining for CD4 or CD8 (PE-conjugated, BD Pharmingen).

Ex vivo Activation and Proliferation Analyses. Splenocytes were stained directly ex vivo for surface expression of activation markers CD25 (PE) and CD62L (APC) in combination with either CD4 or CD8 (FITC)(BD Pharmingen). For BrdU incorporation studies, mice were treated with BrdU (0.8 mg/mouse i.p.) for 3 days prior to analysis. At the indicated time points after infection, mesenteric lymph nodes were isolated and cells were stained for surface expression of CD4 or CD8 prior to fixation. To detect incorporated BrdU, cells were permeabilized with Tween-20 (0.05%), treated with DNAse I solution, and stained with a FITC-conjugated_BrdU mAb (BD Pharmingen).

In Vitro Differentiation of Naive Splenocytes. For in vitro assays, splenocytes were isolated form naive animals, red blood cells lysed using ammonium chloride and depleted of CD8+ and NK1.1_cells by magnetic bead separation (Mullen et al., 2001). Cells were labeled with CFSE (5 µg/ml, Sigma) according to standard protocols (Mullen et al, 2001) and then stimulated with soluble αCD3 antibody (0.1 µg/ml), soluble αCD28 antibody (0.5 µg/ml), and recombinant human IL-2 (10 U/ml, Chiron). For nonpolarizing conditions, cells were cultured with neutralizing antibodies to IL-12 (10 µg/ml) and IL-4 (10 µg/ml). For Th1 polarizing conditions, cultures were supplemented with recombinant mouse IL-12 (5 ng/ml, Genetics Institute) and neutralizing αIL-4 (10 µg/ml) antibody.

First, after 3 days of culture, supernatants were collected to measure IFN-γ concentration by ELISA. Next, the remaining cells were then stimulated with Phorbol 12-myristate 13-acetate (PMA 50 ng/ml, Sigma) and ionomycin (500 ng/ml, Sigma) for 4 hr, treated with BFA (10 µg/ml, Sigma) for 2 hr, and then stained for intracellular IFN-γ in combination with surface CD4 and CFSE incorporation.

In Vitro Signaling Assays. Naive CD4$^+$ CD45RB$^{hi}$ T cells were purified from wild type spleens by FACS sorting (Pflanz et al., 2002). Cells were rested in media overnight and then stimulated with recombinant cytokines for 15 min. Cytokines used were IL-2, 50 ng/ml (R&D Systems); IL-12, 200 ng/ml (R&D Systems); IFN-α, 50 ng/ml (R&D Systems); IFN-γ, 50 ng/ml (R&D Systems); IL-27, 50 ng/ml (DNAX, in-house hyperkines). After stimulation, cells were lysed and probed for total and tyrosine isolated phosphorylated STAT proteins by Western blot (Hibbert et al., 2003). All phospho-STAT antibodies from NEB (Cell Signaling Technology), STAT-1 from Transduction Labs, STAT-3, STAT-4, and STAT-5 from Santa Cruz.

In vivo depletions. Neutralizing αIL-12 mAb, C17.8, αIFN-γ mAb, XMG.6, and αIL-4 mAb, 11B11, 2 mg per dose, were administered intraperitoneally on days 0, 4, 8, and 12 post-infection. Control mice received equivalent amounts of purified rat IgG (Sigma Chemical Co., St. Louis, Mo.).

Lymphocyte proliferation and cytokine assays. Lymphocytes were harvested from MLN, depleted of CD8+ and NK1.1+ cells using magnetic beads in combination with αCD8 and NK1.1 FITC conjugated mAb. Cells were resuspended in RPMI 1640 supplemented with 10% heat-killed fetal bovine serum, 100 U/ml penicillin, 100 g/ml streptomycin, non-essential amino acids and ß-mercaptoethanol, and plated at 4×10⁵ cells/well in 96-well plates. For antigen specific recall responses, cells were cultured alone or in the presence of $T.$ $muris$ Ag, 50 g/ml, for 72 hours. Secreted IL-4, IL-5, IL-13 and IFN-γ was assayed by sandwich ELISA. For detection of intracellular IFN-γ after 14 days of infection, lymphocytes were purified as above, stimulated with αCD3 and αCD28, both 1 g/ml, in the presence of rIL-4, 50 ng/ml, and αIL-12 mAb, C17.8; 10 g/ml. After 72 hours, cells were pulsed with PMA, 50 ng/ml, ionomycin, 500 ng/ml, and Brefeldin A (hereinafter "BfA"), 10 g/ml, for 3-5 hours and stained for intracellular IFN-γ in combination with surface CD4. For detection of intracellular IFN-γ after 21 days of infection, MLN cells were stimulated with αCD3 for 18 hrs and the incubated with BFA for 2 hours before staining for intracellular IFN-γ. Cells were acquired on a FACSCalibur cytometer, and analyzed using CellQuest software. All dot plots shown have a log axis of $10^0$ to $10^4$.

In vitro differentiation assays. Splenocytes were isolated from naVve animals, labeled with CFSE, 5 g/ml, and stimulated for 3-4 days with soluble αCD3 mAb, 0.1 g/ml, soluble αCD28 mAb, 0.5 g/ml, and rIL-2, 10 IU/ml, under Th2 polarizing conditions, rIL-4, 50 ng/ml, and αIL-12 mAb, 10 g/ml, with or without recombinant murine IL-27. For primary stimulations CD4+ T cell proliferation and intracellular IL-4 production were determined by flow cytometry. For secondary stimulations, cells were harvested at day 4, washed and restimulated with αCD3 for 24 hours under neutral conditions. Secreted levels of IL-4, IL-5 and IL-13 were then determined by ELISA.

Estimation of parasite specific IgG2a responses. Parasite-specific IgG2α responses were determined by capture ELISA. Immulon IV plates were coated with $T.$ $muris$ ES Ag, 5 g/ml, in carbonate/bicarbonate buffer overnight at 4 C. After blocking, 3% BSA in PBS, 0.05% Tween, eight serial 2-fold dilutions of sera, from an initial 20-fold dilution, were added to the plates. Parasite-specific antibody was detected using biotinylated rat α-mouse IgG2α in combination with streptavadin-HRP.

Analysis of goblet cell responses. One-centimeter segments of mid-cecum were removed, washed in sterile PBS, and fixed for 24 hours in 10% neutral buffered formalin. Tissues were processed routinely and paraffin embedded using standard histological techniques. Five m sections were cut and stained with haematoxylin and eosin or alcian blue-periodic acid Schiffs for detection of intestinal goblet cells. Enumeration of intestinal goblet cell responses was carried out by counting numbers of goblet cells per 100 crypt units. The anti-mRELMß antibody, its use in immunoblotting, as well as the conditions used to isolate stool proteins have been described previously.

Analysis of mast cell responses for histology. 1 cm lengths of cecum were isolated, washed in PBS and fixed in Carnoy's solution before subsequent processing and sectioning. Mast cells were detected by staining 5 m sections overnight in 0.5° Toluidine Blue in 0.5 mol/liter HCl, pH 0.5, and counterstaining in 1% eosin solution. Enumeration of Toluidine Blue-positive mast cells per 40 fields was carried out for three to four mice per time point. Immunohistochemical detection of MMCP-1+ mast cells was carried out on paraformaldehyfe fixed tissues. Serum mast cell protease-1, MMCP-1, was measured using a commercially available kit.

Growth of mast cells: Passive Cutaneous Anaphylaxis. Mice were anesthetized by intraperitoneal injection of 300 l of 2.5% 2,2,2-tribromoethanol in tert-amyl alcohol:PBS, 1:40. In vivo mast cells were then sensitized with 25 ng of anti-DNP IgE in 25 L of PBS by intradermal injection into the base of the dorsal aspect of the right ear and 25 l of PBS was injection into base of the dorsal aspect the left ear. 24 hours later mice were again anesthetized and challenged with 100 g DNP-HSA in 200 l of 1% Evans blue by intravenous retro-orbital injection. 30 minutes after challenge, mice were euthanized and ears were collected and incubated at 55° C. for 48 hrs in 1 mL of formamide. OD of 300 L of formamide from each sample was then measured at 610 nm in a 96 well plate reader.

Example 1

WSX-1 is Required for Resistance to *Toxoplasma gondii*

To assess the role of IL-27/WSX-1 in the development and regulation of resistance to $T.$ $gondii$, studies were carried out to determine whether infection resulted in increased expression of this cytokine or its receptor. Wild type C57BL/6 mice were inoculated intraperitoneally (i.p.) with 20 cysts of the ME49 strain of $T.$ $gondii$. After 7 days, mRNA was isolated from whole splenocytes of infected and uninfected mice. Reverse transcription PCR (RT-PCR) was used to assess levels of mRNA for IL-27p28, EBI3, and WSX-1 in the spleen. After 7 days of infection, there was an upregulation in levels of mRNA for IL-27p28 and EBI3, while the constitutive level of WSX-1mRNA in unchallenged mice was not appreciably altered by infection (FIG. 1A). To determine the significance of this infection-induced increase of IL-27 mRNA, wild type, WSX-1$^{-/-}$, and IL-12p40$^{-/-}$ mice, n=4 mice per group, representative of three experiments, were infected with $T.$ $gondii$ and their survival monitored. While wild type mice were able to survive the acute phase of this infection, WSX-1$^{-/-}$ animals, like IL-12p40$^{-/-}$ mice, succumbed by day 15 (FIG. 1B). Similar results were observed whether mice were infected orally or intraperitoneally.

Since early mortality of mice deficient in IL-12 is associated with an inability to control parasite numbers, infected WSX-1$^{-/-}$ mice were examined for signs of parasite replication. At 7 days postinfection, peritoneal lavage was performed, cells were collected for cytospin preparation (n=3 per group), and the percentage of cells infected with $T.$ $gondii$ estimated. In contrast to the high parasite burdens found in infected IL-12p40$^{-/-}$ mice, analysis of peritoneal exudates in wild type and WSX-1$^{-/-}$ mice revealed few infected cells and no obvious parasite replication was present in the heart, lungs, spleen, or liver of infected wild type or WSX-1$^{-/-}$ animals (FIG. 1C; data not shown). Wild type and WSX-1$^{-/-}$ animals were infected for 12 days before livers were removed and prepared for histological analysis; in contrast to wild type mice, WSX-1$^{-/-}$ mice developed prominent immune infiltrates and necrosis in the liver and lungs after 12 days of infection (FIGS. 1E-1H; data not shown). Pathology in the liver was further characterized by areas of extramedullary haematopoesis and a loss of hepatocytes leading to the development of telangiectasia (FIG.

1H). Moreover, the spleens of infected WSX-1$^{-/-}$ mice contained disorganized follicular structures and increased numbers of apoptotic cells.

Because previous work has associated CD4$^+$ T cells with the development of lethal immune pathology in experimental models of toxoplasmosis, studies were performed to determine if T cells mediated the acute mortality of infected WSX-1$^{-/-}$ mice. WSX-1-deficient mice were challenged with *T. gondii*, treated with antibodies to deplete CD4$^+$ or CD8$^+$ T cells, and the course of infection was monitored. On days 7, 8, and 9 postinfection, mice were treated with PBS (Ctl.), 500 µg of αCD4 mAB, or 500 µg αCD8 mAb (n=3 per group, representative of three experiments). Although administration of αCD8 on days 5, 6, and 7 postinfection did not alter the time to death of infected WSX-1$^{-/-}$ mice, the same regime using αCD4 prevented early mortality (FIG. 1D). Together, these studies demonstrate that, unlike IL-12p40$^{-/-}$ mice, the enhanced susceptibility of WSX-1$^{-/-}$ mice to *T. gondii* is not due to an inability to control parasite replication, but rather, is a consequence of a CD4$^+$ T cell-dependent immune-mediated pathology.

Example 2

Increased Cytokine Production in WSX-1$^{-/-}$ Mice Infected with *T. gondii*

Figures 2A, 2B, 2C, 2D, 2E, 2F, 2G, 2H, 2I, 2J, 2K, 2L:
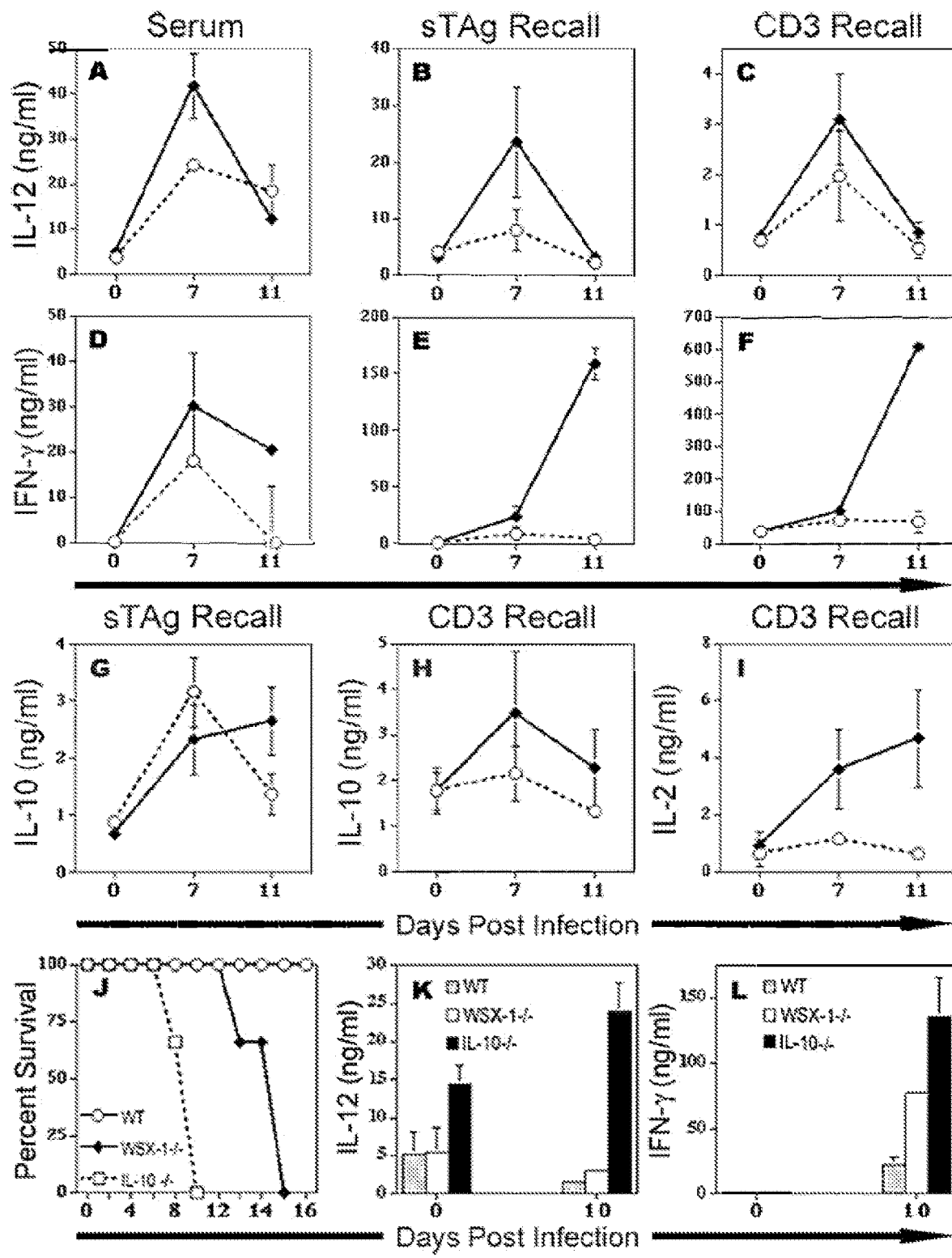
FIG. 2A is a graph which depicts IL-12p40 circulating level at 0, 7, and 11 days postinfection in wild type and WSX-1$^{-/-}$ mice.
FIG. 2B is a graph which depicts IL-12p40 circulating level in splenocytes cultured with soluble $Toxoplasma$ antigen in wild type and WSX-1$^{-/-}$ mice.
FIG. 2C is a graph which depicts IL-12p40 circulating level in splenocytes cultured with plate bound αCD3 antibody in wild type and WSX-1$^{-/-}$ mice.
FIG. 2D is a graph which depicts IFN-γ circulating level at 0, 7, and 11 days postinfection in wild type and WSX-1$^{-/-}$ mice.
FIG. 2E is a graph which depicts IFN-γ circulating level in splenocytes cultured with soluble $Toxoplasma$ antigen in wild type and WSX-1$^{-/-}$ mice.
FIG. 2F is a graph which depicts IFN-γ circulating level in splenocytes cultured with plate bound αCD3 antibody in wild type and WSX-1$^{-/-}$ mice.
FIG. 2G is a graph which depicts IL-10 circulating level in splenocytes cultured with soluble $Toxoplasma$ antigen in wild type and WSX-1$^{-/-}$ mice.
FIG. 2H is a graph which depicts IL-10 circulating level in splenocytes cultured with plate bound αCD3 antibody in wild type and WSX-1$^{-/-}$ mice.
FIG. 2I is a graph which depicts IL-2 production in splenocytes cultured with plate bound αCD3 antibody in wild type and WSX-1$^{-/-}$ mice.
FIG. 2J is a graph which depicts survival of wild type, WSX-1$^{-/-}$, and IL-10$^{-/-}$ mice infected with $T.$ $gondii$.
FIG. 2K is a graph which depicts IL-12p40 concentration in splenocytes from wild type, WSX-1$^{-/-}$, and IL-10$^{-/-}$ mice prior to infection and 10 days postinfection.
FIG. 2L is a graph which depicts IFN-γ concentration in splenocytes from wild type, WSX-1$^{-/-}$, and IL-10$^{-/-}$ mice prior to infection and 10 days postinfection.

To determine how the absence of WSX-1 affected the immune response to *T. gondii*, a kinetic analysis was performed to monitor the production of cytokines associated with resistance to this infection. At 0, 7, and 11 days postinfection (X axes), serum was collected from wild type and WSX-1$^{-/-}$ mice and ELISA used to measure circulating levels of IL-12p40 (A) or IFN-γ (D). At the indicated time points (X-axes), whole splenocytes from wild type and WSX-1$^{-/-}$ mice were cultured with soluble *Toxoplasma* antigen (sTAg, 25 µg/ml) or plate bound αCD3 antibody (1 µg/ml) for 72 hr and assayed for IL-12p40 (B and C), IFN-γ (E and F), IL-10 (G and H) and IL-2 (I) production (n=3 mice per group, representative of three separate experiments). Wild type, WSX-1 and IL-10$^{-/-}$ mice were infected with *T. gondii* and survival was monitored. Infection of wild type and WSX-1$^{-/-}$ mice led to highly elevated serum IL-12 concentrations that were downregulated by day 11 postinfection (FIG. 2A). A similar profile for IL-12 production was obtained by stimulating whole splenocytes from infected mice with soluble *Toxoplasma* antigen (sTAg) or αCD3 (FIGS. 2B and 2C). Likewise, analysis of TNF-α and IL-23 levels in the serum revealed no significant differences between wild type and WSX-1$^{-/-}$ mice. This acute inflammatory response led to a marked increase in systemic IFN-γ levels that, after 7 days, was comparable between wild type and WSX-1$^{-/-}$ mice.

However, by day 11 postinfection, wild type mice had down-regulated serum levels of IFN-γ, whereas WSX-1$^{-/-}$ animals still had high concentrations of circulating IFN-γ (FIG. 2D). A similar trend was observed in splenic recall responses from infected mice. Again, at day 0 and day 7 postinfection, splenocytes from both groups produced similar amounts of IFN-γ when stimulated with sTAg or αCD3 (FIGS. 2E and 2F). At day 11 postinfection, stimulation with sTAg or αCD3 induced WSX-1$^{-/-}$ splenocytes to produce remarkable levels of IFN-γ when compared to wild type cohorts (FIGS. 2E and 2F). In addition, WSX-1$^{-/-}$ splenocytes also produced 4 times as much IL-2 as wild type T cells in these cultures (FIG. 2I).

The phenotype of infected WSX-1$^{-/-}$ mice, particularly the overproduction of IFN-γ associated with lethal immune pathology, is similar to that of IL-10$^{-/-}$ mice challenged with *T. gondii* (FIG. 2J). However, as splenocytes from infected wild type and WSX-1$^{-/-}$ mice produced similar amounts of IL-10 when stimulated with sTAg or αCD3 (FIGS. 2G and 2H), a defect in this regulatory system is unlikely to contribute to the acute mortality of WSX-1$^{-/-}$ mice. Moreover, while WSX-1$^{-/-}$ mice are able to downregulate acute, infection-induced production of IL-12, IL-10$^{-/-}$ mice maintained high levels of this cytokine (FIG. 2K). This distinction between the WSX-1$^{-/-}$ and IL-10$^{-/-}$ mice shows that the enhanced IFN-γ response noted in infected WSX-1$^{-/-}$ mice was not due to the failure of IL-10 to suppress infection induced IL-12 production (FIG. 2L).

Example 3

Enhanced T Cell Responses in *T. gondii*-Infected WSX-1$^{-/-}$ Mice

Figures 3A, 3B:
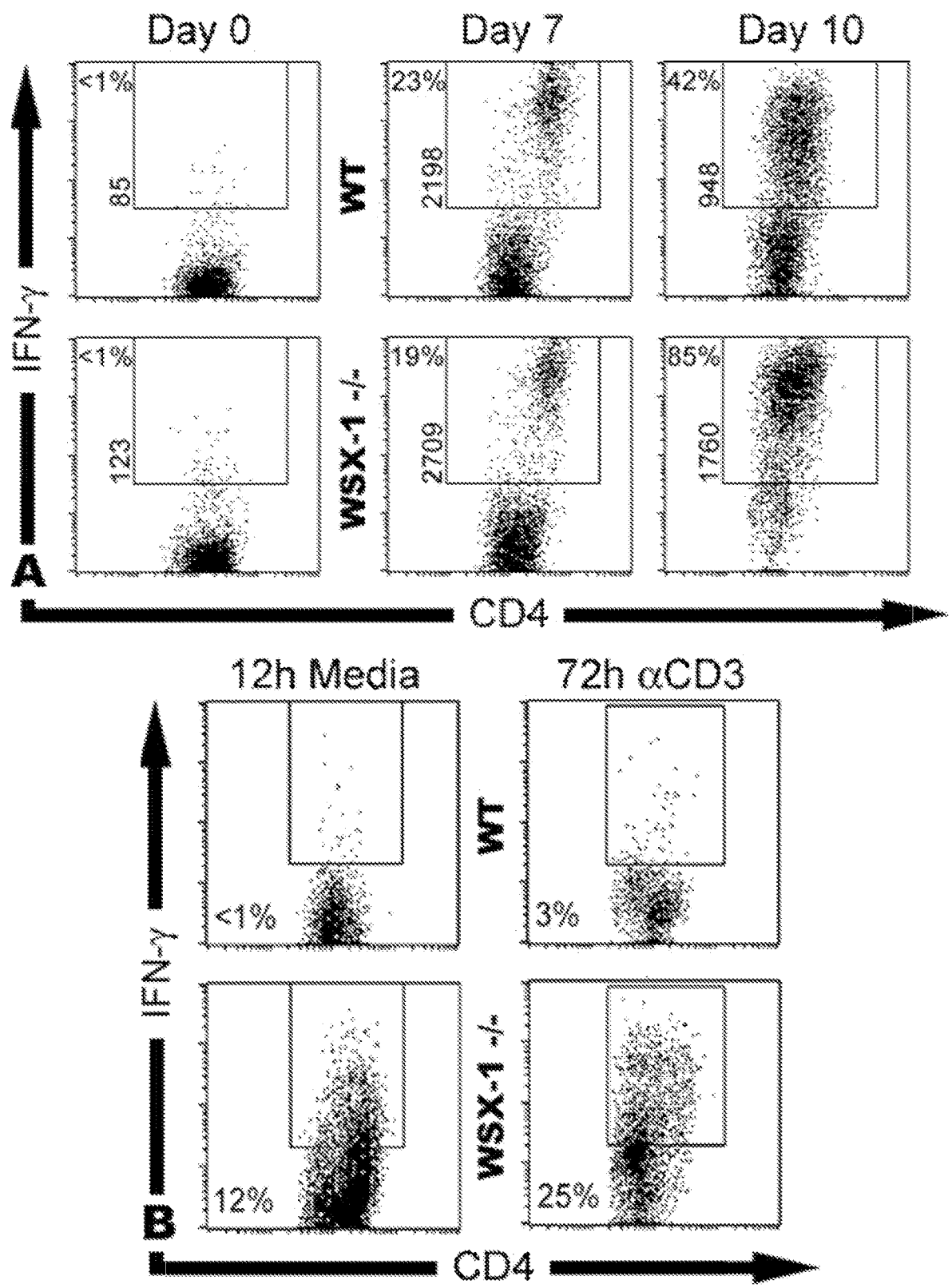
FIG. 3A is a series of flow cytometry photographs which depict splenocytes from wild type and WSX-1$^{-/-}$ mice infected for 0, 7, and 10 days, and stained for CD4 and intracellular IFN-γ.
FIG. 3B is a series of flow cytometry photographs which depict splenocytes from wild type and WSX-1$^{-/-}$ mice infected for 11 days, and stained for CD4 and intracellular IFN-γ.

Since CD4$^+$ T cells are involved in the susceptibility of WSX-1$^{-/-}$ mice to acute toxoplasmosis and splenocytes from infected WSX-1-deficient mice secreted elevated levels of IFN-γ, single cell analysis was utilized to assess IFN-γ production by T cells. Splenocytes from wild type and WSX-1$^{-/-}$ mice infected for 0, 7, and 10 days were isolated and stimulated with plate bound αCD3 antibody for 18 hr before staining for CD4 and intracellular IFN-γ. CD4$^+$ T cells from uninfected wild type and WSX-1$^{-/-}$ mice produced little IFN-γ after 18 hr of stimulation with αCD3 and at 7 days postinfection, a similar percentage of cells produced IFN-γ in both wild type and WSX-1$^{-/-}$ animals (FIG. 3A). However, by 11 days postinfection 2-fold more WSX-1$^{-/-}$ CD4$^+$ T cells were producing IFN-γ when compared to wild type cohorts (85% versus 42%) (FIG. 3A). Moreover, CD4$^+$ T cells from 10 day infected WSX-1$^{-/-}$ mice produced more cytokine per cell than wild type cells (FIG. 3A). While wild type splenocytes required ex vivo stimulation to produce IFN-γ, 12.0% of CD4$^+$ T cells from WSX-1$^{-/-}$ mice stained positive for IFN-γ after 12 hr of culture in media alone (FIG. 3B). Splenocytes were isolated from wild type and WSX-1$^{-/-}$ mice that were infected with *T. gondii* for 11 days. Cells were either rested in media for 12 hr or stimulated with αCD3 antibody for 72 hr, before staining for CD4 and intracellular IFN-γ. For flow cytometry, only CD4$^+$ events are displayed and rectangular gates indicate specific IFN-γ staining compared to control mAb; the percentage of IFN-γ$^+$ cells are oriented horizontally while mean fluorescence intensity (MFI) values are oriented vertically. WSX-1$^{-/-}$ Th1 cells were also able to maintain IFN-γ production for longer than their wild type counterparts. When stimulated with αCD3 for 72 hr, 25% of CD4$^+$ T cells from 14 day infected WSX-1$^{-/-}$ mice were still secreting IFN-γ, while few wild type IFN-γ producers remained (FIG. 3B).

Figures 4A, 4B:
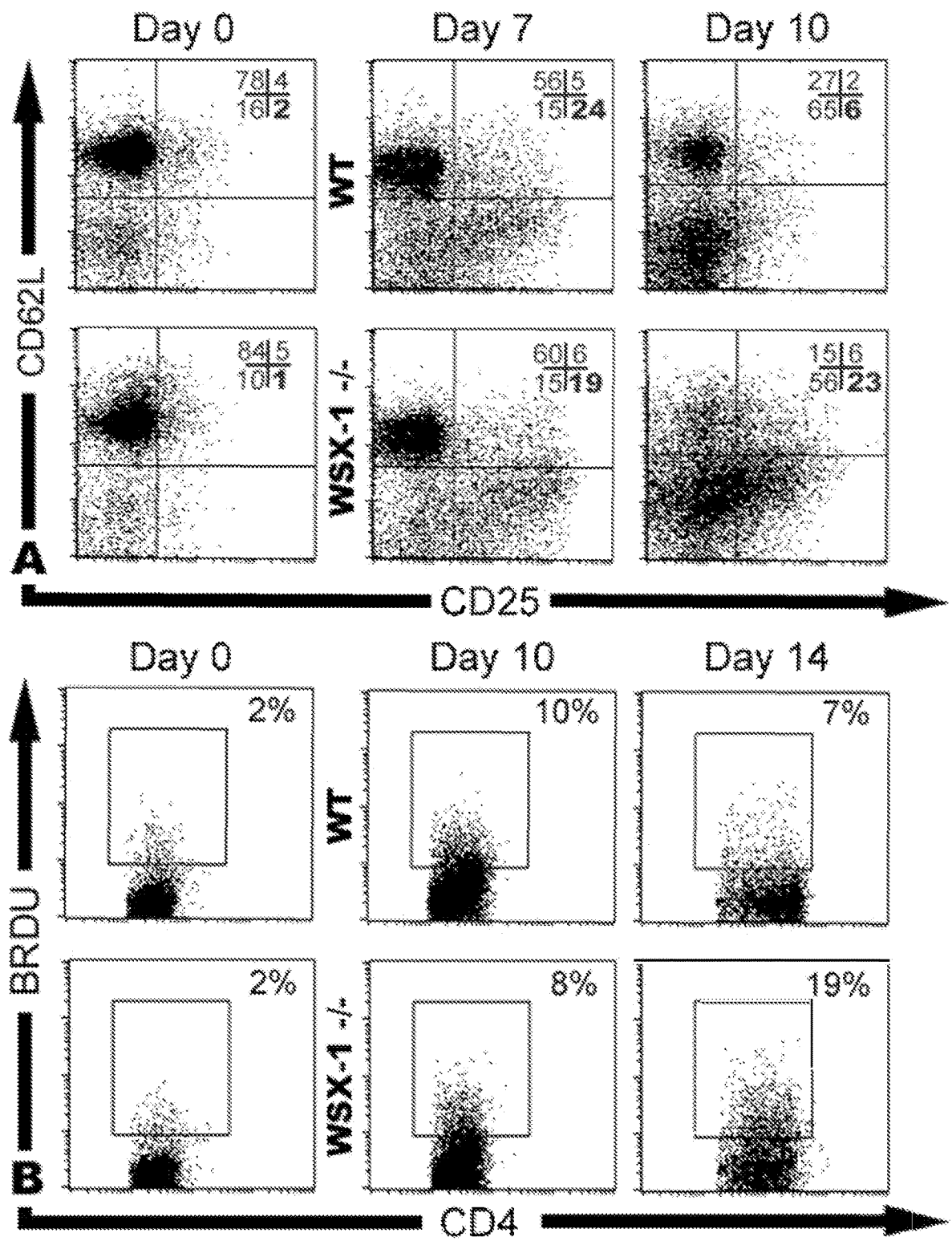
FIG. 4A is a series of flow cytometry photographs which depict splenocytes from wild type and WSX-1$^{-/-}$ mice infected for 0, 7, and 10 days, stained for expression of CD4, CD25, and CD62L.
FIG. 4B is a series of flow cytometry photographs which depict splenocytes from wild type and WSX-1$^{-/-}$ mice infected and treated for 3 days prior to sacrifice at days 0, 10, and 14 postinfection, stained for CD4 expression and incorporation of BrdU.

To further assess how the development of the T cell response was affected by the absence of WSX-1, receptor-deficient mice were infected with *T. gondii* and the expression of various activation markers by T cells was determined. Wild type and WSX-1$^{-/-}$ mice were infected for 0, 7, and 10 days before splenocytes were isolated and stained for expression of CD4, CD25, and CD62L directly ex vivo. Numbers in the figures represent the percentage of CD4$^+$ cells in each indicated quadrant with the percentage of CD25high/CD62Llow in bold type. In accord with the production of IFN-γ shown in FIGS. 2 and 3, by day 7 postinfection, a comparable rise in the number of activated T cells (CD25high/CD62Llow) was observed in wild type and WSX-1$^{-/-}$ mice (FIG. 4A). While the number of activated T cells in wild type mice was decreased after 10 days of infection, consistent with decreased production of IFN-γ and a general downregulation of the anti-*Toxoplasma* response, the frequency of CD25high/CD62Llow CD4$^+$ T cells in WSX-1$^{-/-}$ mice increased further (FIG. 4A). A similar profile for the production of IFN-γ and expression of activation markers was observed for CD8$^+$ T cells from infected WSX-1$^{-/-}$ mice.

Although there were elevated numbers of activated T cells in WSX-1$^{-/-}$ mice infected with *T. gondii*, the basis of this accumulation remained unclear. Since previous reports have shown that WSX-1$^{-/-}$ CD4$^+$ T cells have enhanced proliferative responses in vitro, studies were performed to evaluate in vivo proliferation of WSX-1$^{-/-}$ T cells. Wild type and WSX-1$^{-/-}$ mice were infected orally with *T. gondii* and treated with BrdU for 3 days prior to sacrifice at days 0, 10, and 14 postinfection, and, at different times postinfection, the incorporation of this synthetic nucleotide was determined in CD4$^+$ T cells. Wild type and WSX-1$^{-/-}$ mice were infected for 0, 7, and 10 days before splenocytes were isolated and stained for expression of CD4, CD25, and CD62L directly ex vivo. Numbers represent the percentage of CD4$^+$ cells in each indicated quadrant with the percentage of CD25high/CD62Llow in bold type. Again, as with IFN-γ production and activation marker expression, the amount of BrdU incorporated was comparable between wild type and WSX-1$^{-/-}$ CD4$^+$ lymphocytes at days 0 and 10 postinfection (FIG. 4B). After 2 weeks, suppression of the wild type immune response was reflected in decreased numbers of CD4$^+$ T cells that had incorporated BrdU. In contrast, at this later time point, the population of WSX-1$^{-/-}$ CD4$^+$ T cells that had incorporated BrdU continued to expand (FIG. 4B). This enhanced proliferative response, a phenomenon previously reported in vitro, is likely to contribute to the accumulation of pathogenic CD4$^+$ T cells occurring during acute *T. gondii* infection of WSX-1$^{-/-}$ mice. Together, these studies indicate that while WSX-1 is not necessary for the generation of highly activated Th1 effector T cells following challenge with *T. gondii*, this receptor is required to regulate the intensity and duration of infection induced Th1 responses.

Example 4

WSX-1$^{-/-}$ T Cells Exhibit Intrinsic Hyperactivity after Infection with *T. gondii*

Figures 5A, 5B, 5C:
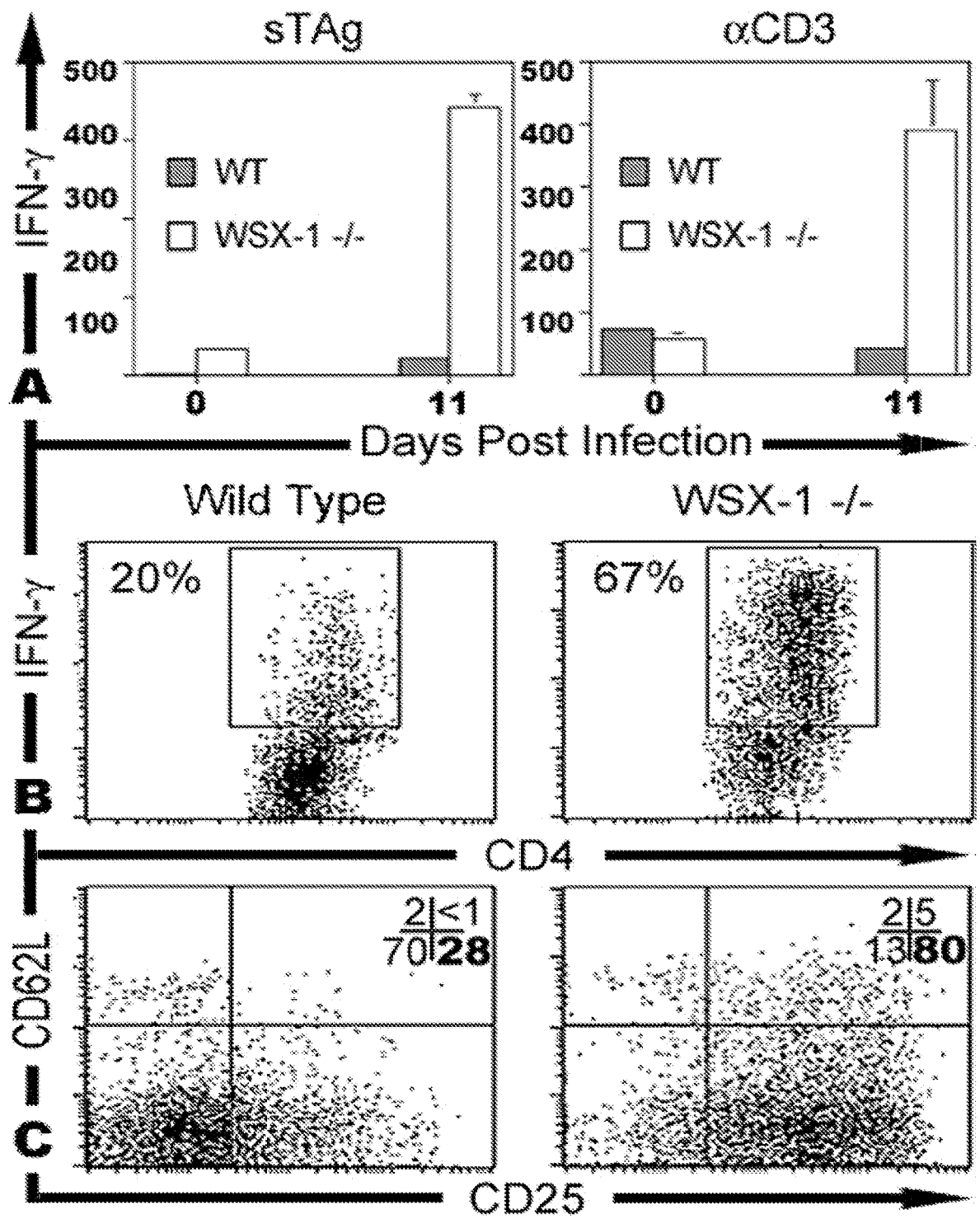
FIG. 5A is a pair of graphs which depict IFN-γ production in wild type or WSX-1$^{-/-}$ cells adoptively transferred into RAG-2$^{-/-}$ mice.
FIG. 5B is a pair of flow cytometry photographs which depict splenocytes isolated at 11 days postinfection, and stained for CD4 and intracellular IFN-γ.
FIG. 5C is a pair of flow cytometry photographs which depict splenocytes isolated at 11 days postinfection, and stained for expression of CD4, CD25, and CD62L.

Although infection with *T. gondii* led to an expanded population of activated Th1 cells in WSX-1$^{-/-}$ mice, it was unknown whether this enhanced persistence was cell autonomous or mediated through altered accessory cell function. To address this issue, splenocytes were isolated from uninfected mice, depleted of adherent cells, and 75×10$^6$ wild type or WSX-1$^{-/-}$ cells were adoptively transferred into RAG-2$^{-/-}$ mice. Seven days later, mice were infected with *T. gondii* and at 11 days postinfection, whole splenocytes from wild type and WSX-1$^{-/-}$ mice were cultured with soluble *Toxoplasma* antigen or plate bound αCD3 antibody for 72 hr and assayed for IFN-γ production by ELISA (ng/ml). At day 11 postinfection, splenocytes were isolated and stained for expression of CD4, CD25, and CD62L directly ex vivo. Numbers represent the percentage of CD4$^+$ cells in each indicated quadrant with the percentage of CD25high/CD62Llow in bold type. Analysis of T cell responses in these reconstituted mice revealed that, as in infected WSX-1$^{-/-}$ mice, adoptively transferred WSX-1$^{-/-}$ T cells produced elevated levels of IFN-γ during recall responses (FIG. 5A). Furthermore, WSX-1$^{-/-}$ CD4$^-$ T cells were 3 times more likely to produce IFN-γ (67% versus 20%) and had increased expression of activation markers when compared to wild type cohorts (FIGS. 5B and 5C). These data indicate that the hyperactivity that follows infection is intrinsic to the T cells and not due to defects in the accessory cell compartment of WSX-1$^{-/-}$ mice.

Example 5

WSX-1 is not Required for In Vitro Th1 Differentiation

In contrast to the data presented above, previous reports suggested that IL-27/WSX-1 is required for optimal Th1 differentiation. Therefore, in vitro studies were performed to further assess the impact of WSX-1 deficiency on CD4$^+$ T cell responses. Naive CD4$^+$ T cells were purified from uninfected wild type or WSX-1$^{-/-}$ spleens, stained with CFSE, and activated with soluble αCD3 (0.1 µg/ml) and αCD28 (0.5 µg/ml) under either (A) nonpolarizing conditions (α-IL-12 and α-IL-4) or (B) Th1 polarizing conditions (rIL-12 plus α-IL-4). First, after hr of culture, supernatants were collected and secreted levels of IFN-γ determined by ELISA. Then, remaining cells from the same cultures were stimulated with PMA and ionomycin for 4 hr before performing intracellular staining for IFN-γ in combination with CFSE and CD4. Based on CFSE profiles, the number of cells in each individual generation was calculated and data are presented in each table for wild type and WSX-1$^{-/-}$ T cells under neutral (A) and Th1 (B) polarizing conditions. RT-PCR analysis revealed increased expression of IL-27p28 and EBI3 mRNA in all cultures, indicating the likely presence of IL-27 in these studies. When naive, wild type CD4$^+$ T cells were activated under nonpolarizing conditions (αIL-4, αIL-12), a small percentage of wild type cells became competent to produce IFN-γ and a low concentration of protein was detected in the supernatants (FIG. 6A). In parallel cultures, a reduced percentage of WSX1$^{-/-}$ CD4$^+$ T cells stained positive for IFN-γ while almost no IFN-γ was secreted (FIG. 6A). By using CFSE labeling to track cell divisions, a small but reproducible increase in the ability of WSX-1$^{-/-}$ CD4$^+$ T cells to proliferate was noted (FIG. 6A). Thus, in accord with previous studies, IL-27/WSX-1 is crucial for the optimal production of IFN-γ by naive CD4$^+$ T cells that have been activated under nonpolar conditions. However, a role for IL-27/WSX-1 in the regulation of other effector functions was demonstrated by a small but reproducible increase in the ability of WSX-1$^{-/-}$ CD4$^+$ T cells to proliferate (FIG. 6A).

When naive wild type and WSX-1$^{-/-}$ CD4$^+$ T cells were differentiated under Th1 polarizing (αIL-12, αIL-4), there was no significant difference in the percentage of wild type and WSX-1$^{-/-}$ cells that produced IFN-γ (FIG. 6B). However, analysis of supernatants from the same cultures revealed that WSX1$^{-/-}$ CD4$^+$ T cells secreted 2 to 3 times more IFN-γ than wild type cohorts (FIG. 6B).

Moreover, a marked increase in proliferation was also noted in CD4$^+$ T cells from the WSX-1$^{-/-}$ cultures (FIG. 6B). These data indicate that, when activated under Th1 conditions, a similar frequency of IFN-γ wild type and WSX-1$^{-/-}$ T cells arise, but due to enhanced proliferation, more total WSX-1-deficient IFN-γ cells accumulate thereby leading to a significant increase in the secreted protein concentrations. Thus, in the presence of strongly polarizing IL-12 concentrations in vitro or during in vivo infection with *T. gondii*, the ability of IL-27/WSX-1 to augment IFN-γ production becomes redundant. Furthermore, these data demonstrate that, while IL-27/WSX-1 plays an important role in the regulation of several effector functions, like proliferation and cytokine production, WSX-1-deficient CD4$^+$ T cells do not have an intrinsic defect in Th1 differentiation.

Example 6

IL-27 Signaling Leads to Heterogeneous STAT Activation

The data presented above demonstrate that both wild type and WSX-1$^{-/-}$ mice develop a vigorous, protective Th1 type response following infection with *T. gondii*, but while wild type mice can downregulate this response, WSX-mice are unable to do so. Furthermore, the failure to downregulate CD4$^+$ T cell responses contributes to the infection-induced mortality in WSX-1$^{-/-}$ mice. While these studies provide a cellular mechanism for the severe immune pathology observed in WSX-1$^{-/-}$ mice (FIG. 1H), they are inconsistent with previous studies that showed that recombinant IL-27 could enhance CD4$^+$ T cell IFN-γ responses. Therefore, to explore the basis for the stimulatory and inhibitory effects of IL-27/WSX-1 on T cell function, naive CD45RBHi CD4$^+$ T cells were treated with rIL-27 in vitro and the signaling pathways activated by this cytokine were examined. Naive CD4$^+$ CD45RB$^{hi}$ T cells were sorted from wild type spleens, rested overnight, and then stimulated with r IFN-γ, IFN-γ, or rIL-27 (all 50 ng/ml) for 15 min. Cells were then lysed and total or tyrosine phosphorylated STAT-1, STAT-3, and STAT-5 were detected by Western blot. Based on structural homology of WSX-1 with other class I cytokine receptors, it was likely that IL-27 would activate the Jak/STAT signaling pathway. Cells were stimulated with various cytokines and the ability to phosphorylate STATs 1, 3, and 5 was assessed. Stimulation of naive CD4$^+$ T cells with IL-2 or IL-12 failed to activate STAT1, STAT3, or STAT5, while exogenous IFN-α and IFN-γ resulted in activation of STAT1 and STAT3 but not STAT5.

Figure 7:
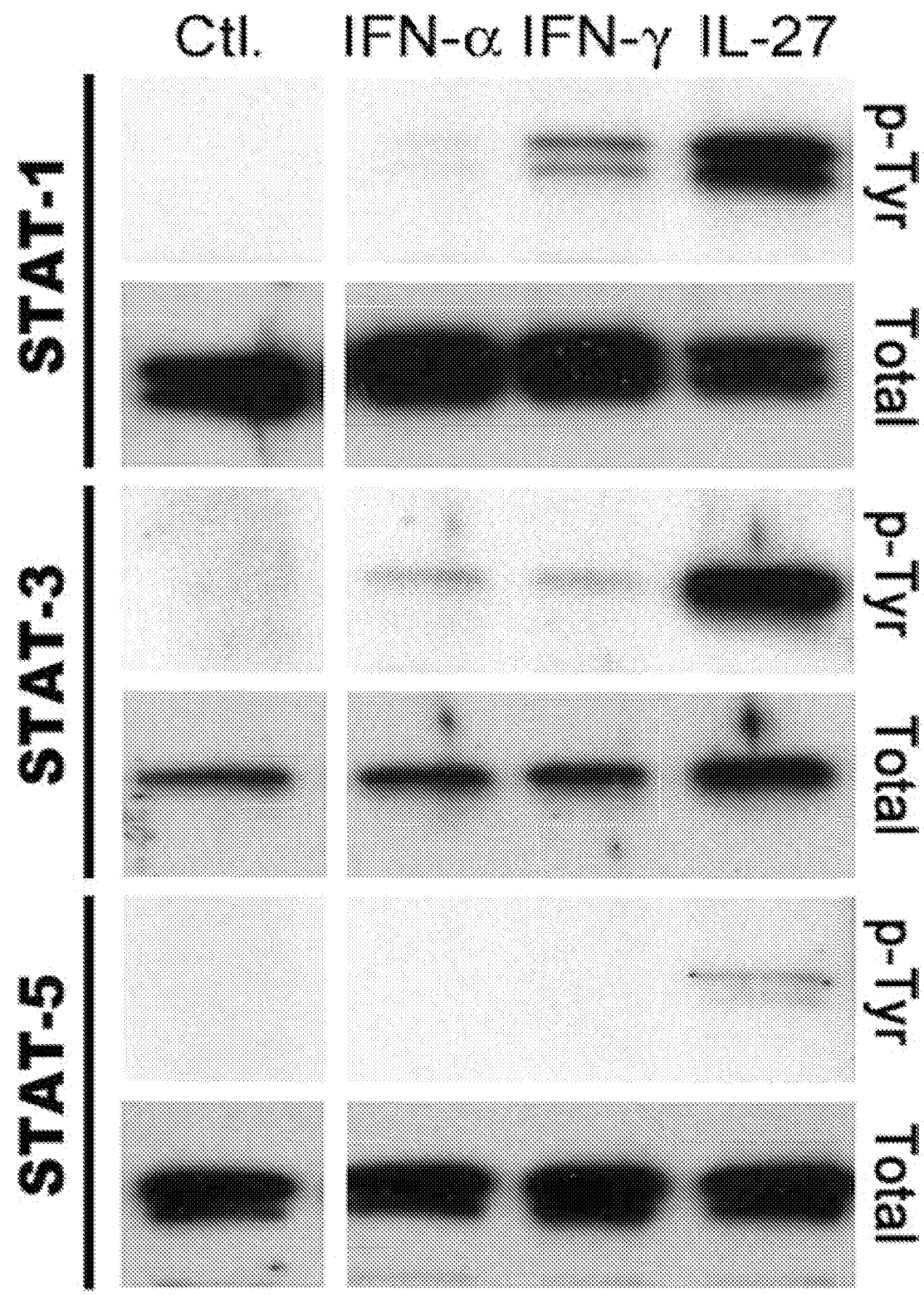
FIG. 7 is a photograph of a Western blot which depicts total and tyrosine phosphorylated STAT-1, STAT-3, and STAT-5 detected following stimulation of naive CD4+ CD45RB$^{hi}$ T cells with rIFN-γ, IFN-γ, or rIL-27.
Figure 8:
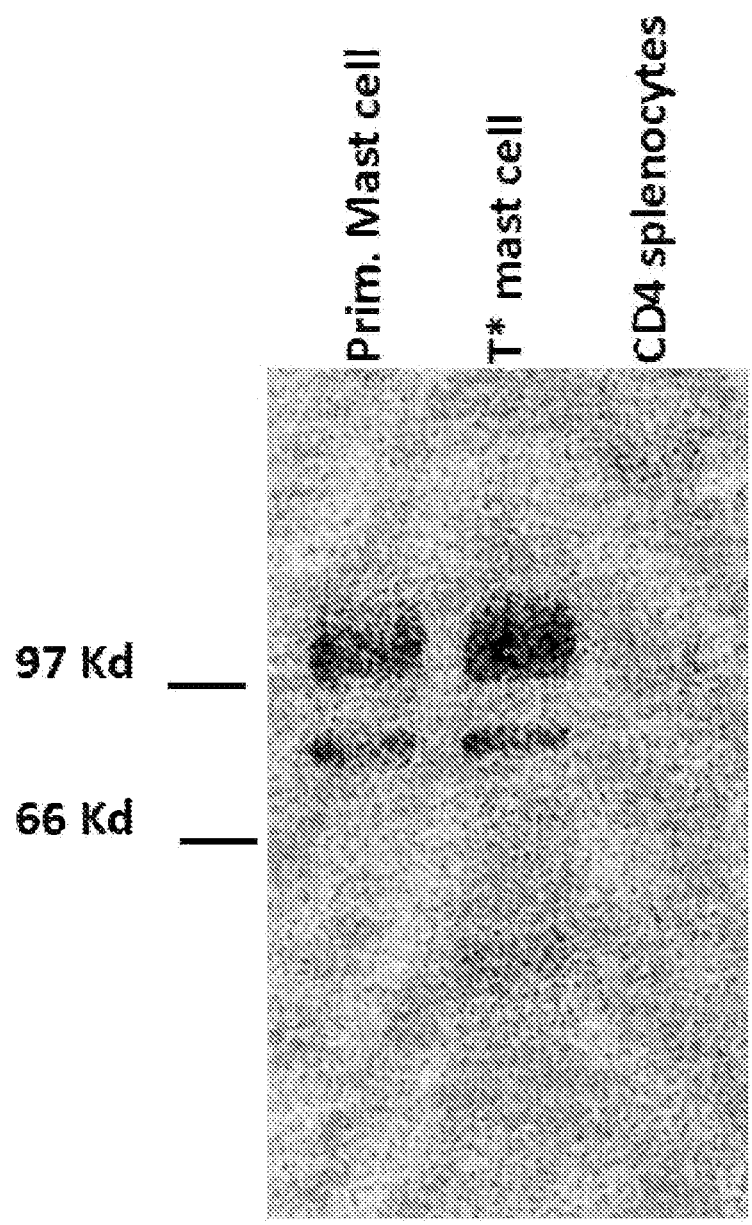
FIG. 8 is a photograph that depicts primary bone marrow-derived mouse mast cells, a spontaneously immortalized BM-derived mouse mast cell line (T*) or CD4+ splenocytes (9×10e6) which were immunoprecepitated with antibody against WSX-1. The blot was probed with the same anti-WSX-1 Ab.
Figure 9:
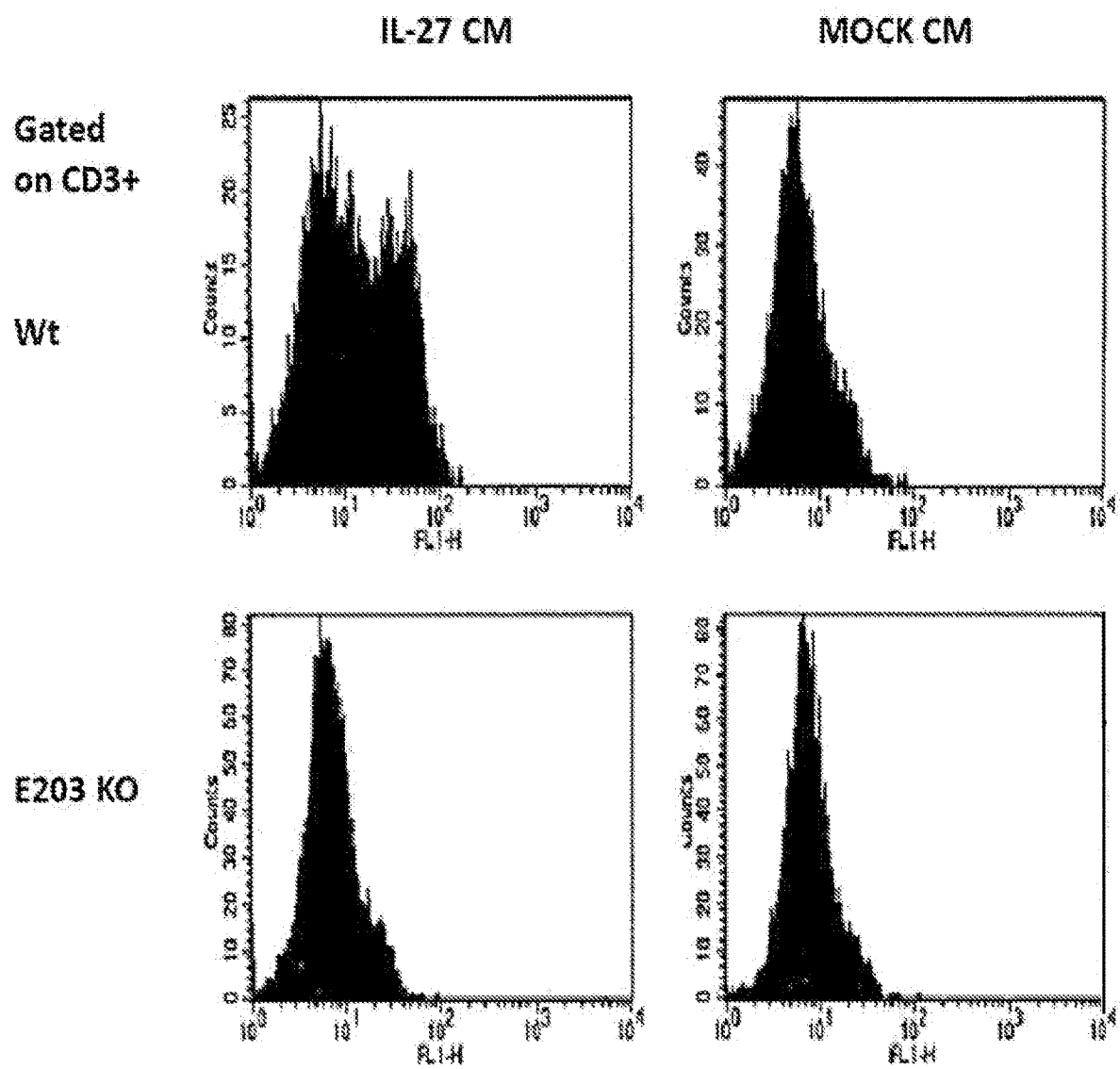
FIGS. 9-13 are graphs which depict a Flow Cytometry analysis of whole blood from wild type and WSX-1 knock-out mice stimulated with conditioned medium from either mock-transfected or IL-27-transfected 293 cells. The cells are stained for intracellular phospho-STAT1 as a measure of IL-27 signaling and a surface maker to identify the cell lineage of the responding cells (CD3+ in FIG. 9, GR-1+ in FIG. 10, CD11b+ in FIG. 11 and CD4+ in FIG. 13). The data show that, in whole blood, two major cell types respond: CD4 T cells (FIG. 13) and a cell type that is currently characterized by its scatter properties only (FIG. 12), but appears to be of non-lymphoid nature: mast cells or possibly basophils. This data shows that these two major cell types not only express IL-27 receptor, but that IL-27R is functionally competent on both cell types.
Figure 10:
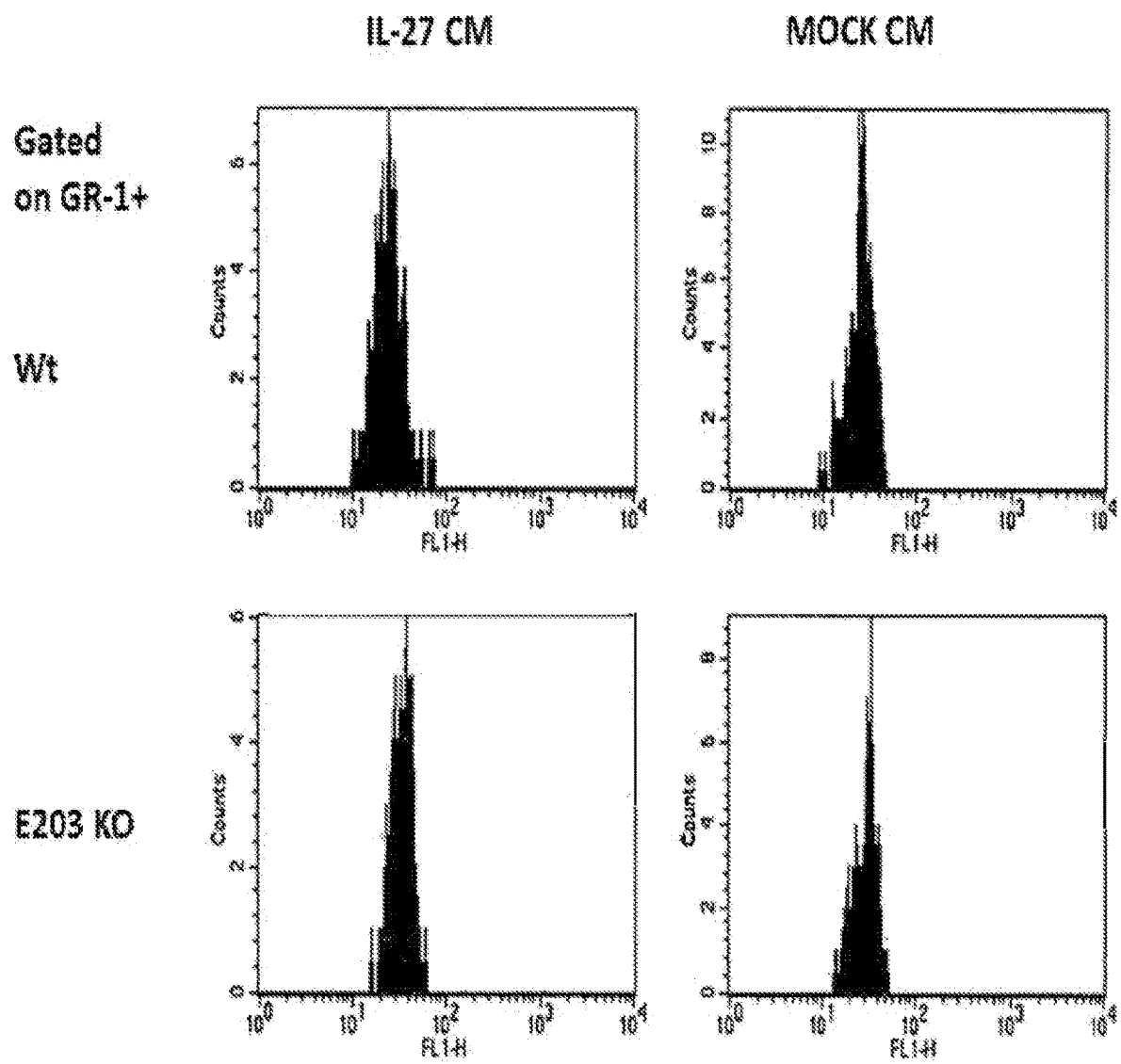
Figure 11:
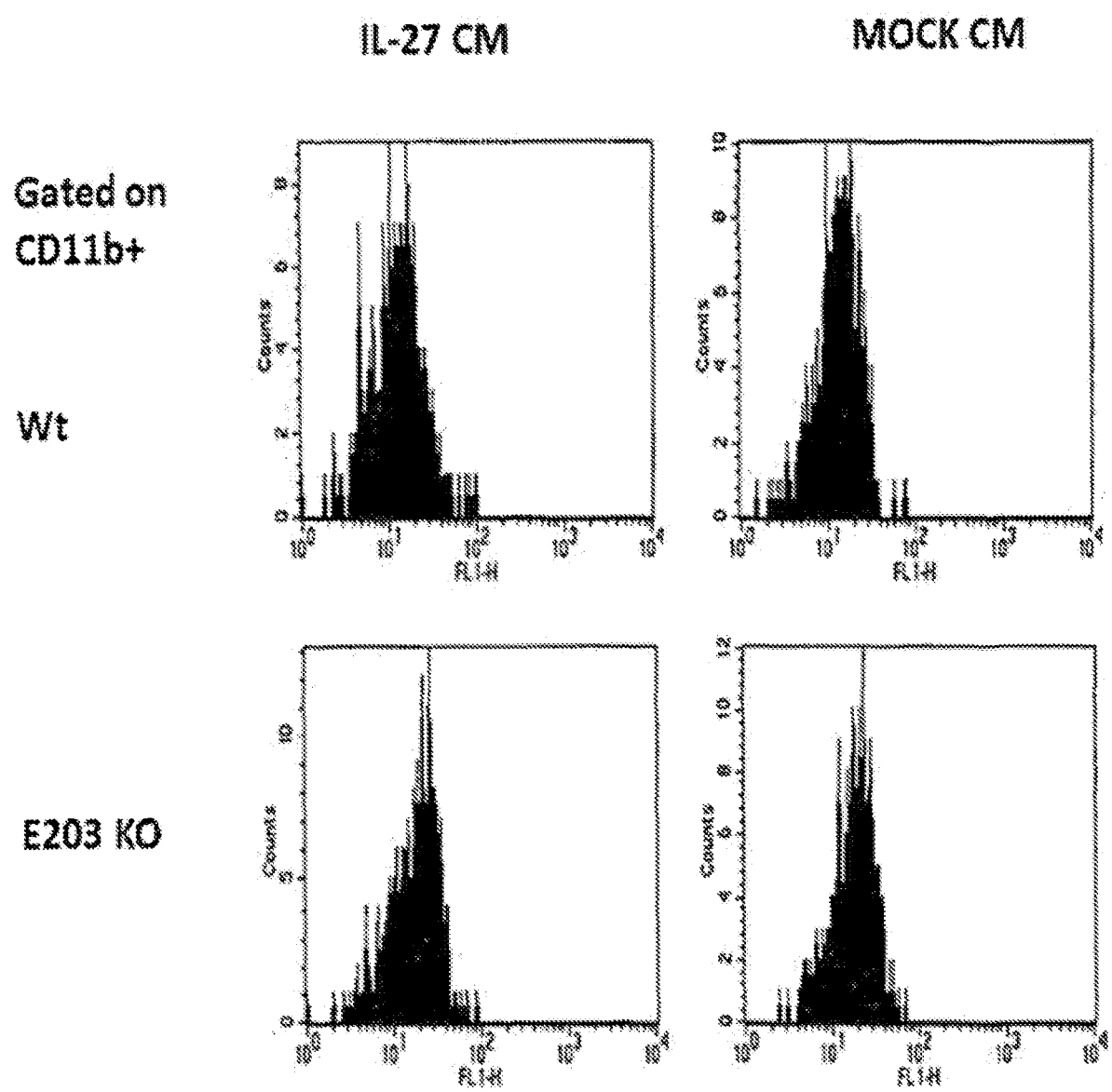
Figure 12:
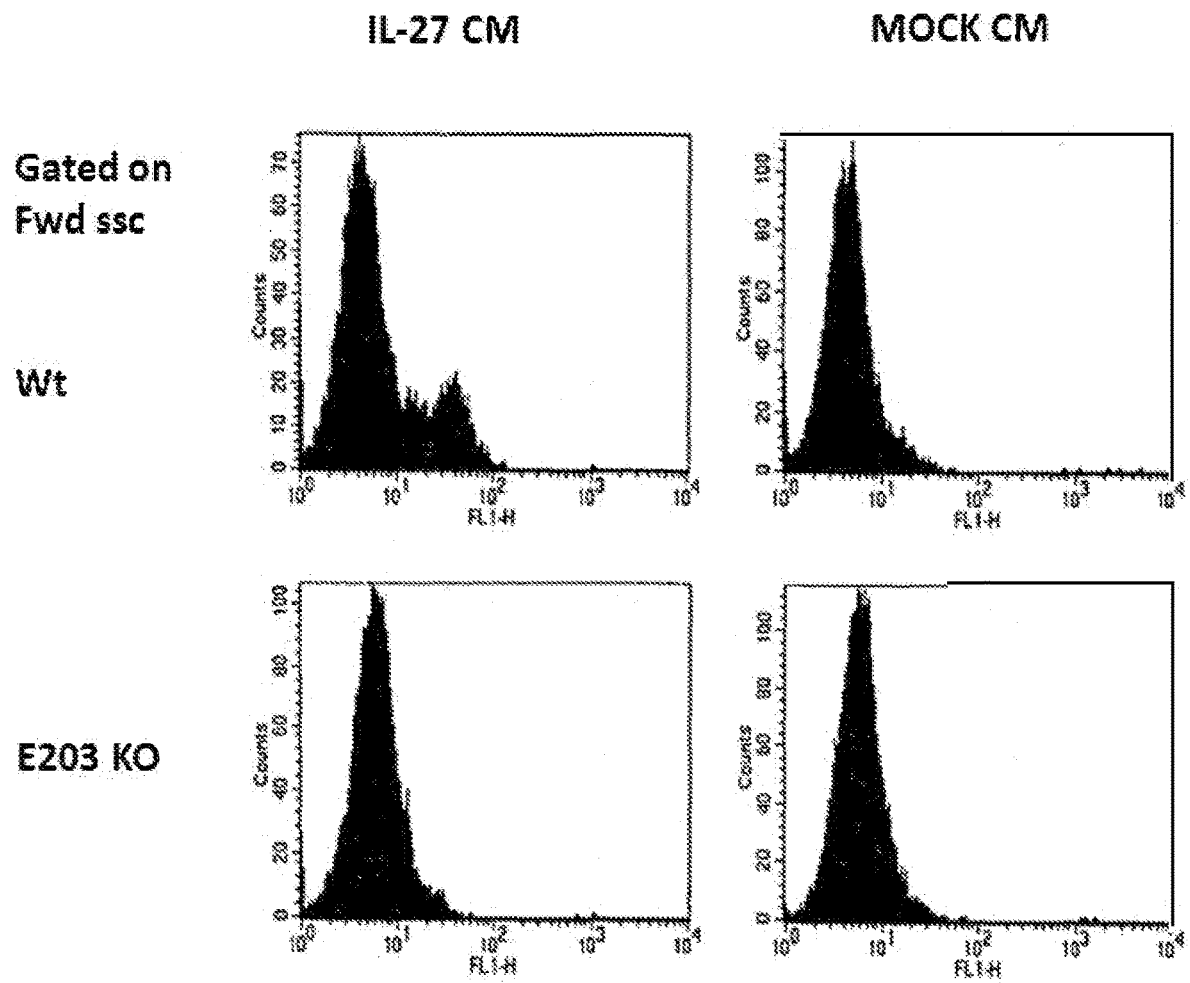
Figure 13:
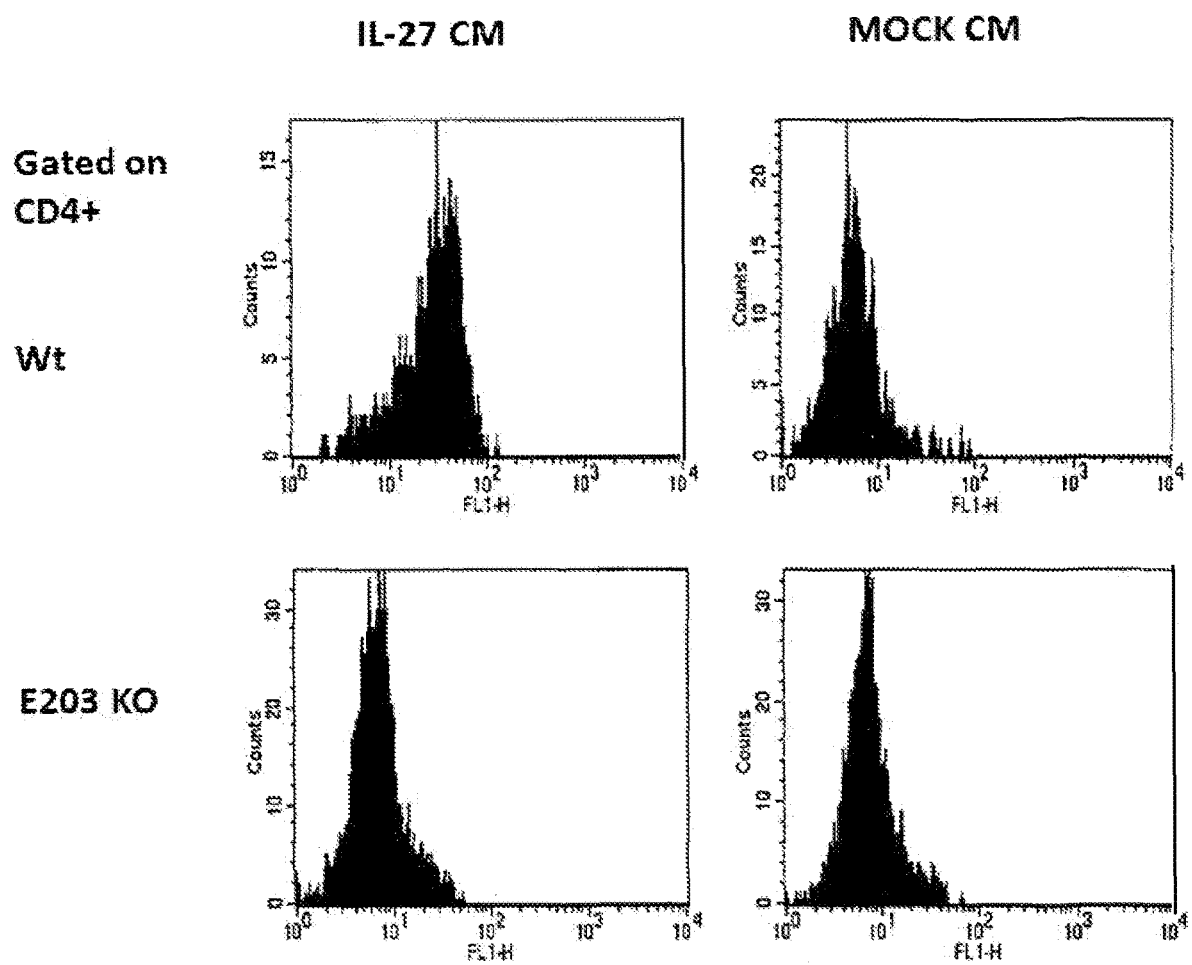

In contrast, stimulation with IL-27 led to increased tyrosine phosphorylation of STAT1, STAT3, and STAT5 (FIG. 7). These data are in accord with recent reports that WSX-1 signaling leads to STAT-1 phosphorylation (Hibbert et al., 2003; Takeda et al., 2003), but the finding that IL-27 can also activate STAT3 and STAT5 in naive CD4$^+$ T cells extends our knowledge of the signaling pathways used by IL-27/WSX-1.

Example 7

Infection with *T. muris* Leads to Increased IL-27 mRNA Expression

Previous studies demonstrated that macrophage and DC lineages increase expression of IL-27 mRNA following LPS stimulation. In addition, upregulation of IL-27/WSX-1 mRNA has been reported in vivo following infection with the protozoan pathogen *T. gondii*. However, little was known about expression of IL-27/WSX-1 following exposure to Th2-inducing stimuli such as infection with helminth parasites. Wild type C57B/6 mice were infected orally with *T. muris*, and after 0 (i.e. uninfected), 7, and 14 days post-infection, mRNA was isolated from MLN and RT-PCR performed to quantify expression of IL-27p28, EBI3, WSX-1 and ß-actin. Wild type and WSX-1$^{-/-}$ mice were infected with *T. muris* for 14 days and the intestinal larval worm burden determined by microscopy. Wild type and WSX-1$^{-/-}$ mice were infected with *T. muris* for 14 days, MLN cells isolated and stimulated with *T. muris* antigen, 50 g/ml, for 48 hours. Concentrations of secreted IL-4 and IL-5 were determined by ELISA. Oral challenge of wild type C57BL/6 mice with *T. muris* resulted in the generation of a protective Th2 response which leads to worm expulsion between day 18-21 post-infection. The use of RT-PCR to analyze levels of mRNA for WSX-1, EBI3 and IL-27p28 mRNA in the draining MLN of C57BL/6 mice on days 0, 7, and 14 post-infection revealed that while levels of mRNA for WSX-1 and EBI3 was constitutive, there was a marked increase in the levels of IL-27p28 mRNA following *T. muris* infection. Together, these data demonstrate that in response to infection with *T. muris* there is the production of IL-27 that may regulate the immune response to this parasite.

Example 8

Infection of WSX-1$^{-/-}$ Mice Leads to Accelerated Worm Expulsion Mediated by Enhanced Th2 Responses To assess the role of the IL-27/WSX-1 interaction in immunity to *T. muris*, wild type C57BL/6 and WSX-1$^{-/-}$ mice were inoculated with infective eggs and the worm burden measured at day 21 post-infection. At this time point, wild type C57BL/6 mice had expelled worms and WSX-1$^{-/-}$ mice displayed a similar phenotype. Although these data demonstrated that WSX-1$^{-/-}$ mice can develop protective immunity to *T. muris*, it was unclear if the absence of WSX-1 affected the kinetics of this response. Therefore, wild type and WSX-1$^{-/-}$ mice were challenged with *T. muris* and worm burden assessed at day 14 post-infection. At this time point, infected wild type mice harbored high numbers of *T. muris*, indicating that protective Th2 responses had not yet been established. In contrast, at this early time point, infected WSX-1$^{-/-}$ mice had expelled larval parasites.

To determine if enhanced resistance to *T. muris* in WSX-1$^{-/-}$ mice was associated with increased Th2 responses, MLN cells were isolated from wild type and WSX-1$^{-/-}$ mice at day 14 post-infection and parasite-specific cytokine responses analyzed. MLN cells from infected WSX-1$^{-/-}$ mice secreted significantly higher levels of IL-4 and IL-5 compared to cells from infected wild type mice. To confirm that the enhanced resistance to *T. muris* observed in WSX-1$^{-/-}$ mice was due to a type 2 effector cytokine response, αIL-4 mAb was administered to infected WSX-1$^{-/-}$ mice. After 14 days of infection, treatment with αIL-4 led to the equivalent establishment of infection in wild type and WSX-1$^{-/-}$ mice. These data indicate that in WSX-1$^{-/-}$ mice, elevated Th2 responses mediate enhanced resistance to *T. muris*.

Example 9

Enhanced Goblet Cell and Mast Cell Responses in the Absence of WSX-1

We have established that the development of protective Th2 type responses required for resistance to *T. muris* are associated with a goblet cell hyperplasia and mastocytosis. To better understand the basis for the enhanced resistance of WSX-1$^{-/-}$ mice to *T. muris* several approaches were used to compare intestinal goblet cell and mast cell responses in wild type and WSX-1$^{-/-}$ mice. Analysis of histological sections of gut tissue mice stained to visualize goblet cells mucin revealed that in uninfected wild type and WSX-1$^{-/-}$ mice, similar numbers of goblet cells were observed. However at day 14 post-infection, while wild type mice displayed no signs of infection-induced goblet cell hyperplasia, WSX-1$^{-/-}$ mice demonstrated a dramatic increase in intestinal goblet cell hyperplasia and mucin production.

To further characterize these goblet cell responses, western blots and immunohistochemistry were used to examine the expression of RELMß, a goblet cell specific protein that is stimulated during Th2 responses. These studies revealed that while uninfected wild type mice expressed negligible levels of REW uninfected WSX1$^{-/-}$ mice expressed higher levels of this protein. Furthermore, following 14 days of infection wild type mice expressed low levels of this protein and WSX-1$^{-/-}$ mice displayed a marked elevation in the levels of RELMß. Together, these studies demonstrate that WSX-1$^{-/-}$ mice display enhanced goblet cell responses following infection with *T. muris* and these data are consistent with the elevated Th2 responses and enhanced resistance to this parasite in these mice.

Analysis of histological sections stained to visualize intestinal mast cells revealed that uninfected wild type and WSX-1$^{-/-}$ mice had similar numbers of mast cells. After 14 days of infection, mid-cecum sections were stained for detection of intestinal goblet cells and the number of goblet cells per 100 crypt units enumerated by microscopy. At 14 days post-infection in wild type mice these numbers were not significantly increased whereas at this time point, WSX-1$^{-/-}$ mice displayed a marked increase in mast cell numbers. This infection-induced mastocytosis was accompanied by elevated serum levels of mast cell protease that was not observed in wild type mice at the same time point. These data establish that WSX-1$^{-/-}$ mice infected with *T. muris* develop a strong mast cell response that correlates with the establishment of a parasite-specific Th2 response and enhanced resistance to this parasite. While it seemed likely that the mastocytosis observed in infected WSX-1$^{-/-}$ mice would be a consequence of the enhanced Th2 responses, a comparison of the levels of WSX-1 on mast cell and splenic CD4$^+$ T cells revealed that mast cells expressed high levels of WSX-1 and these results indicated that WSX-1 may have a direct role in the regulation of mast cell function.

To more directly assess the role of WSX-1 in the regulation of mast cell response in vivo, wild type and WSX-1$^{-/-}$ mice were used to assay mast cell responses in an IgE-mediated mast cell dependent model of passive cutaneous anaphylaxis. In these studies, wild type and WSX-1$^{-/-}$ mice were primed with intradermal injections of anti-DNP-IgE and challenged 24 hours later with DNP-BSA in a solution of Evans blue. Rechallenge leads to anaphylaxis and the rapid release of mast cell derived mediators that results in profound changes in vascular permeability and the extravasation of Evans blue provides a surrogate marker of plasma exudation. In these assays, rechallenge led to the extravasation of Evans blue in wild type mice but these levels were significantly increased in the absence of WSX-1: wild type, n=11; WSX-1$^{-/-}$, n=10, p=0.0036 Student T test. Taken together these studies demonstrate that WSX-1 can act as a negative regulator of mast cell responses.

Example 10

Enhanced Th2 Responses and Rapid Expulsion of *T. muris* in WSX-1$^{-/-}$ Mice are Independent of a Defect in IFN-γ Production Together, the studies discussed above demonstrate that WSX-1$^{-/-}$ mice develop enhanced resistance to *T. muris*, but these findings do not address the mechanism that underlies the elevated Th2 responses. Since IL-27/WSX-1 can promote the production of IFN-γ, it is possible that a primary defect in Th1 responses in WSX-1$^{-/-}$ mice would lead to unopposed Th2 responses in infected mice. This hypothesis is supported by studies demonstrating that IL-12 and IFN-γ can impair the development of protective Th2 cytokine responses following chronic infection with *T. muris*.

To address whether a defect in the production of IFN-γ contributed to the enhanced Th2 responses in infected WSX-1$^{-/-}$ mice, the ability of MLN cells from wild type or WSX-1$^{-/-}$ mice infected for 14 days to produce IFN-γ was assessed. MLN cells from wild type and WSX-1$^{-/-}$ mice infected for 14 days were isolated and stimulated with αCD3/αCD28 for 48 hours as described above. Cells were stained for intracellular IFN-γ in combination with surface CD4. In these experiments, stimulation with *T. muris* Ag resulted in the production of negligible levels of IFN-γ. However, stimulation of MLN cells from these animals with αCD3 revealed that there was a higher frequency of WSX-1$^{-/-}$ CD4$^+$ T cells producing IFN-γ when compared to wild type controls. These findings demonstrate that there was no early defect in the production of IFN-γ in WSX-1-mice infected with *T. muris* and are consistent with recent reports that identified WSX-1-independent IFN-γ responses in vivo. Nevertheless, to address whether a defect in IFN-γ production would result in accelerated type 2 immunity, studies were performed to assess how the absence of a Th1 response would affect cytokine production and worm expulsion in wild type mice infected with *T. muris*.

Wild type mice were treated with αIL-12 plus αIFN-γ prior to and during infection and response monitored at day 14 post-infection. Wild type mice were challenged with *T. muris* and treated with neutralizing αIL-12 and αIFN-γ mAb, 2 mg/dose, on days 0, 4, 8 and 12 post-infection. After 14 days of infection, MLN cells were isolated from untreated wild type, untreated WSX-1$^{-/-}$, and mAb treated wild type mice. For all groups, mean intestinal larval worm burden was determined by microscopy, and are representative of three independent experiments. Cells were stimulated with *T. muris* Ag and the concentrations of secreted IL-5 and IL-13 quantified by ELISA. In these studies, the administration of αIL-12 and αIFN-γ resulted in a small increase in the production of IL-5 and IL-13, but these levels were markedly lower than those observed in WSX-1$^{-/-}$ mice. Moreover, in contrast to WSX-1$^{-/-}$ mice, treatment with αIL-12 plus αIFN-γ did not result in goblet cell hyperplasia, enhanced expression of RELMß, or rapid expulsion of *T. muris*. Similar results were obtained when IFN-γ$^{-/-}$ mice were challenged with *T. muris*. Together, these studies demonstrate that the enhanced type 2 responses observed in the WSX-1$^{-/-}$ mice are not reproduced following in vivo blockade of Th1 responses in wild type mice and demonstrate that the enhanced Th2 responses observed in WSX-1$^{-/-}$ mice infected with *T. muris* are independent of a defect in IFN-γ production.

Example 11

Inhibition of Th2 Responses by IL-27/WSX-1 In Vitro

Although the data presented above demonstrate an enhanced Th2 response in WSX-1$^{-/-}$ mice infected with *T. muris*, it was unclear whether this was due to a direct effect on T cell function. To address this issue, studies were performed to determine how the absence of WSX-1 or the addition of IL-27 affected the development of CD4+ T cell responses under Th2 polarizing conditions, in which endogenous Th1 responses are blocked.

NaVve wild type and WSX-1$^{-/-}$ splenocytes were stimulated with αCD3 plus αCD28 under Th2 polarizing conditions, αIL-12, rIL-4, and CD4+ T cell proliferation and cytokine production assayed. Polyclonal stimulation was associated with increased levels of IL-27 mRNA in these cultures and sustained expression of mRNA for WSX-1 in wild type cells, suggesting the presence of functional IL-27/WSX-1 signaling in vitro. For primary stimulations, wild type and WSX-1$^{-/-}$ splenocytes were isolated from uninfected mice and activated with soluble αCD3/αCD28 under Th2 polarizing conditions. After 72 hours, cells were stained for intracellular IL-4 in combination with surface CD4. After three days of primary stimulation, intracellular staining for IL-4 revealed that there were equivalent frequencies of wild type and WSX-1$^{-/-}$ CD4+ T cells that were IL-4+.

For secondary stimulations, wild type or WSX-1$^{-/-}$ splenocytes were activated as above for 96 h, washed, counted, and restimulated with plate bound αCD3, 1 g/ml, under neutral conditions. After 24 hours, secreted concentrations of IL-5 and IL-13 were determined by ELISA. For proliferation assays, naVve wild type and WSX-1$^{-/-}$ splenocytes were labeled with CFSE before undergoing primary stimulation as before. Upon secondary stimulation of these cells, although negligible levels of IL-4 protein were detected, there was a significant increase in the production of IL-5 and IL-13 in WSX-1$^{-/-}$ compared to wild type cultures. After 3 or 4 days in culture, CD4+ T cell proliferation was visualized by flow cytometry. The number of cells in proliferative generations 1 through 6 are enumerated for primary stimulations of 3 or days. Results are representative of four independent experiments. Analysis of the proliferative response during primary stimulation revealed that there were increased numbers of WSX-1$^{-/-}$ CD4+ T cells present in the 1st to the 4th proliferative generations on day 3 after stimulation. By day 4 post-stimulation, the enhanced proliferative responses of WSX-1$^{-/-}$ CD4+ T cells over wild type controls were even more apparent, with a marked increase in the percentage of WSX-1$^{-/-}$ T cells observed in the 5th and 6th generations. Furthermore, the CD4+ T cell responder frequency, an indicator of the percentage of cells that have responded to antigenic stimulation by undergoing at least one proliferative cycle, was higher in WSX-1$^{-/-}$ compared to wild type cultures: wild type, 34%; WSX-1$^{-/-}$, 46%. Consistent with the enhanced Th2 responses observed in the absence of WSX-1, when recombinant IL-27 was added to cultures of wild type CD4+ T cells, a marked reduction in the levels of IL-4 being produced was observed. However, in these experiments these effects were not associated with a reduction on the levels of proliferation. Taken together, these in vitro studies indicate that the IL-27/WSX-1 interaction is a negative regulator of Th2 effector cell function and is the basis for the enhanced Th2 responses observed in WSX-1$^{-/-}$ mice following infection with *T. muris*.

Figure 14:
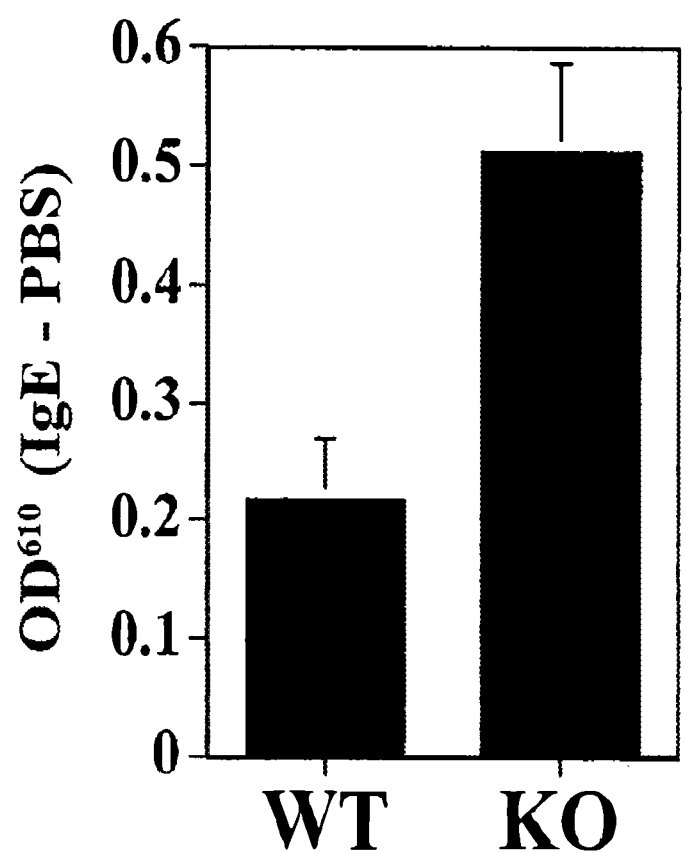
FIG. 14 is a histogram showing the OD read at 610 nm, a measure of vascular permeability, for whole blood from wild type and WSX-1 knockout mice stimulated with conditioned medium from either mock-transfected or IL-27-transfected 293 cells.

FIGS. 9-13 are graphs which depict a Flow Cytometry analysis of whole blood from wild type and WSX-1 knockout mice stimulated with conditioned medium from either mock-transfected or IL-27-transfected 293 cells. The cells are stained for intracellular phospho-STAT1 as a measure of IL-27 signaling and a surface maker to identify the cell lineage of the responding cells. The data show that, in whole blood, two major cell types respond; CD4 T cells and a cell type that is currently characterized by its scatter properties only, but appears to be of non-lymphoid nature: mast cells or possibly basophils. FIG. 14 shows the OD read at 610 nm, a measure of vascular permeability. This data shows that these two major cell types not only express IL-27 receptor, but that IL-27R is functionally competent on both cell types.

The invention being thus described, it will be obvious that the same may be modified or varied in many ways. Such modifications and variations are not to be regarded as a departure from the spirit and scope of the invention and all such modifications and variations are intended to be included within the scope of the following claims.

We claim:
1. A method for increasing a T-helper cell mediated immune response in an animal, which comprises selecting an animal requiring immunostimulation as a result of cancer or chemotherapy; and administering to said animal an effective amount of an IL-27R antagonist that prevents functional activation of IL-27R by IL-27, wherein said antagonist is an antibody that binds to IL-27, an antibody that binds to EBI3, an antibody that binds to IL27p28, or an antibody that binds to IL-27R.
2. The method of claim 1, wherein said T-helper cell is Th1.
3. The method of claim 1, wherein said T-helper cell is Th2.
4. The method of claim 1, wherein the functional activation is IL-27 signaling.
5. The method of claim 1, wherein the animal is a human.

* * * * *